US008148607B2

(12) United States Patent
D'Halluin et al.

(10) Patent No.: US 8,148,607 B2
(45) Date of Patent: Apr. 3, 2012

(54) METHODS AND MEANS FOR REMOVAL OF A SELECTED DNA SEQUENCE

(75) Inventors: Kathleen D'Halluin, Mariakerke (BE); Rene Ruiter, Heusden (BE)

(73) Assignee: Bayer CropScience N.V., Diegem (BE)

( * ) Notice: Subject to any disclaimer, the term of this patent is extended or adjusted under 35 U.S.C. 154(b) by 1090 days.

(21) Appl. No.: 11/910,515

(22) PCT Filed: Mar. 31, 2006

(86) PCT No.: PCT/EP2006/003086
§ 371 (c)(1), (2), (4) Date: Oct. 2, 2007

(87) PCT Pub. No.: WO2006/105946
PCT Pub. Date: Oct. 12, 2006

(65) Prior Publication Data

US 2009/0089890 A1 Apr. 2, 2009

Related U.S. Application Data

(60) Provisional application No. 60/669,243, filed on Apr. 7, 2005.

(30) Foreign Application Priority Data

Apr. 4, 2005 (EP) .................................... 05075781

(51) Int. Cl.
*C12N 15/82* (2006.01)

(52) U.S. Cl. .................................... 800/288; 435/320.1

(58) Field of Classification Search ........................ None
See application file for complete search history.

(56) References Cited

U.S. PATENT DOCUMENTS

| | | | | |
|---|---|---|---|---|
| 6,013,859 | A | 1/2000 | Fabijanski et al. | |
| 6,407,314 | B1 | 6/2002 | Oldenhof et al. | |
| 6,861,576 | B1 | 3/2005 | Drouaud et al. | |
| 7,736,886 | B2 * | 6/2010 | Puchta et al. | 435/254.11 |
| 2005/0060769 | A1 | 3/2005 | Gilbertson | |
| 2005/0172365 | A1 | 8/2005 | Puchta et al. | |

FOREIGN PATENT DOCUMENTS

| | | |
|---|---|---|
| CN | 1249133 | 4/2000 |
| EP | 0317509 | 5/1989 |
| EP | 0790311 | 2/1996 |
| WO | 94/17176 | 8/1994 |
| WO | 94/18313 | 8/1994 |
| WO | 95/09233 | 4/1995 |
| WO | 96/14408 | 5/1996 |
| WO | 97/30166 | 8/1997 |
| WO | WO 97/30166 | * 8/1997 |
| WO | 00/46386 | 8/2000 |
| WO | 01/36595 | 5/2001 |
| WO | WO 03/004659 | * 1/2003 |
| WO | 03/080809 | 10/2003 |
| WO | 2004/067736 | 8/2004 |
| WO | 2005/049842 | 6/2005 |
| WO | 2006/032426 | 3/2006 |

OTHER PUBLICATIONS

Orel N. et al. Different pathways of homologous recombination are used for the repair of double-strand breaks within tandemly arranged sequences in the plant genome. The Plant Journal, vol. 35, No. 5. (2003), pp. 604-661).*

Miao Z.H. et al. Targeted disruption of the TGA3 locus in *Arabidopsis thaliana*. Plant J. Feb. 1995;7(2):359-65.*

Albani, et al., "A *Brassica napus* gene family which shows sequence similarity to ascorbate oxidase is expressed in developing pollen. Molecular characterization and analysis of promoter activity in transgenic tobacco plants," *The Plant Journal*, 2(3) :331-342 (1992).

Chilton and Que, Targeted Integration of T-DNA into the Tobacco Genome at Double-Stranded Breaks: New Insights on the Mechanism of T-DNA Integration, *Plant Physiology*, 133: 956-965 (2003).

Colleaux, et al., "Recognition and cleavage site of the intron-encoded *omega* transposase," *Proc. Natl. Acad. Sci. USA* (*Genetics*) 85: 6022-6026 (1988).

Hohn, et al., "Elimination of selection markers from transgenic plants," *Current Opinion in Biotechnology*, 12 :139-141 (2001).

Isalan, et al., "A rapid, generally applicable method to engineer zinc fingers illustrated by targeting the HIV-1 promoter," *Nature Biotechology*, 19 :656-660 (2001).

Kalderon, et al., "A Short Amino Acid Sequence Able to Specify Nuclear Location," *National Institute for Medical Research*, (*Biochemistry Division*) :499-510 (1984).

Kumar and Fladung, "Controlling transgene integration in plants," *Trends in Plant Science*, 6(4):155-159 (2001).

Liu, et al., "Design of polydactyl zinc-finger proteins for unique addressing within complex genomes," *Proc. Natl. Acad. Sci. USA* (*Biochemistry*) 94: 5525-5530 (1997).

Needleman and Wunsch, "A General Method Applicable to the Search for Similarities in the Amino Acid Sequence of Two Proteins," *J. Mol. Biol*. 48: 443-453 (1970).

Paszkowski, et al, "Gene targeting in plants," *The EMBO Journal*, 7(13): 4021-4026 (1988).

Puchta, et al., "Two different but related mechanisms are used in plants for the repair of genomic double-strand breaks by homologous recombination," *Proc. Natl. Acad. Sci. USA* (*Genetics*), 93: 5055-5060 (1996).

Puchta, "Marker-free transgenic plants," *Plant Cell, Tissue and Organ Culture*, 74 :123-134 (2003).

Raikhel, "Nuclear Targeting in Plants," *Plant Physiology*, 100: 1627-1632 (1992).

(Continued)

*Primary Examiner* — Cynthia Collins
(74) *Attorney, Agent, or Firm* — Hunton & Williams LLP

(57) ABSTRACT

A method is described for the exact removal of a selected subfragment from a DNA molecule by intrachromosomal recombination between two directly repeated DNA sequences using a rare-cleaving double stranded break inducing DNA endonuclease expressed under control of a microspore specific promoter. This method can be applied in a method for the exact exchange of a target DNA fragment for a DNA fragment of interest in plant cells and plants.

14 Claims, 6 Drawing Sheets

OTHER PUBLICATIONS

Salomon and Puchta, "Capture of genomic and T-DNA sequences during double-strand break repair in Somatic plant cells," *The EMBO Journal*, 17(20): 6086-6095 (1988).

Siebert and Puchta, "Efficient Repair of Genomic Double-Strand Breaks by Homologous Recombination between Directly Repeated Sequences in the Plant Genome," *The Plant Cell*, 14 :1121-1131 (2002).

Tzfira, et al., "Site-Specific Integration of *Agrobacterium tumefaciens* T-DNA via double-Stranded Intermediates," *Plant Physiology*, 133: 1011-1023 (2003).

* cited by examiner

Cont'd on Fig 2B

Continuation from Fig 2A

↓ Cross with receptor plant via pollen

↓ Selection of progeny for presence of SGM2

↓ Screening of progeny for absence of SGM1

MSP   DSBIE2  3'   SMG2

↓ Cross with receptor plant

↓ Screening of progeny for absence of SGM2

METHODS AND MEANS FOR REMOVAL OF A SELECTED DNA SEQUENCE

CROSS-REFERENCE TO RELATED APPLICATIONS

This application is the U.S. National Stage filing of International Application No. PCT/EP2006/003086, filed Mar. 31, 2006, which claims benefit of European Patent Application No. 05075781.4, filed Apr. 4, 2005, and U.S. Provisional Patent Application No. 60/669,243, filed Apr. 7, 2005, the disclosures of each of which are hereby incorporated by reference.

BACKGROUND OF THE INVENTION

1. Field of the Invention

The current invention relates to method and means that allow the efficient removal of a selected part of a DNA sequence of interest previously introduced into said plant, such as e.g. a selectable or screenable marker gene without resorting to in vitro culture during the removal step. The removal method can be used as part of a method for exact exchange in plant cells and plants of a target DNA sequence for a DNA sequence of interest through homologous recombination, whereby the selectable or screenable marker used during the homologous recombination phase for temporal selection of the gene replacement events can subsequently be removed without leaving a foot-print and without resorting to in vitro culture during the removal step.

2. Background Art

The removal of selected sub-fragments of foreign DNA introduced into plant cells or plants, but which have subsequently become obsolete or even unwanted, for various reasons, after introduction thereof, has been the subject of intensive research. Examples of such sequences are e.g. selectable marker genes which were necessary for the isolation of transgenic plants but which are no longer required in the mature plants. Methods to achieve efficient elimination thereof mostly rely on site-specific recombination or transposition (see e.g. Hohn et al., Plant BioTechnology pp 139-143).

Siebert and Puchta (2002) described that transgenic sequences flanked by sites of a rare cutting restriction enzyme can be excised efficiently from the genome of a higher eukaryote by homologous recombination as well as by non-homologous end-joining.

WO03/004659 relates to recombination systems and to a method for removing nucleic acid sequence from the chromosomal DNA of eukaryotic organisms. The document also relates to transgenic organisms (preferably plants), containing the described systems or produced by the described methods.

However the described methods mostly require the use of an in vitro culture method to identify or select those plant cells in which the deletion of the DNA sequences to be removed has effectively taken place and to regenerate a plant from such cells.

U.S. patent application 2005/0060769 proposes a method to prepare a recombined transgenic *Zea mays* plant or plant cell from a first transgenic *Zea mays* plant cell, wherein the transgene in the recombinant plant or plant cell has an altered genetic structure relative to the genetic structure of the transgene in the first transgenic plant cell, due to homologous recombination-mediated transgene deletion.

Hereinafter, including in the claims, different embodiment of methods and means for the efficient removal of selected subsequence of a part of a DNA molecule previously introduced in the cells of a plant without having to resort to in vitro culture methods, are described.

WO97/30166 or U.S. Pat. No. 6,407,314 describe promoter fragments from a microspore-specific gene from tobacco that can be used for expression of genes in microspores.

Another problem that has been solved by the present invention concerns the targeted and exact exchange through homologous recombination of a target DNA sequence in a cell of a plant for a replacement DNA sequence without leaving footprints of the procedure, and without having to resort to in vitro culture methods after the initial step of homology recombination. To this end, the herein described methods for efficient removal of selected subsequence of a part of a DNA molecule previously inserted in the genome, preferably the nuclear genome of cells of a plant, through intrachromosomal homologous recombination can be conveniently used.

The need to control the site of transgene integration in plants has been recognized early on, and several methods have been developed in an effort to meet this need (for a review see Kumar and Fladung, 2001, Trends in Plant Science, 6, pp 155-159). These methods mostly rely on homologous recombination-based transgene integration, a strategy which has been successfully applied in prokaryotes and lower eukaryotes (see e.g. EP0317509 or the corresponding publication by Paszkowski et al., 1988, EMBO J., 7, pp 4021-4026). However, for plants, the predominant mechanism for transgene integration is based on illegitimate recombination which involves little homology between the recombining DNA strands. A major challenge in this area is therefore the detection of the rare homologous recombination events, which are masked by the far more efficient integration of the introduced foreign DNA via illegitimate recombination.

One way of solving this problem is by selecting against the integration events that have occurred by illegitimate recombination, such as exemplified in WO94/17176.

Another way of solving the problem is by activation of the target locus through the induction of double stranded DNA breaks via rare-cutting endonucleases, such as I-SceI. This technique has been shown to increase the frequency of homologous recombination by at least two orders of magnitude using *Agrobacteria* to deliver the repair DNA to the plant cells (Puchta et al., 1996, Proc. Natl. Acad. Sci. U.S.A., 93, pp 5055-5060).

WO96/14408 describes an isolated DNA encoding the enzyme I-SceI. This DNA sequence can be incorporated in cloning and expression vectors, transformed cell lines and transgenic animals. The vectors are useful in gene mapping and site-directed insertion of genes.

WO00/46386 describes methods of modifying, repairing, attenuating and inactivating a gene or other chromosomal DNA in a cell through I-SceI double strand break. Also disclosed are methods of treating or prophylaxis of a genetic disease in an individual in need thereof. Further disclosed are chimeric restriction endonucleases.

Chilton and Que (2003, Plant Physiol. 133: pp 956-965) and Tzifira et al. (2003, Plant Physiol. 133: pp 1011-1023) report that T-DNA preferentially integrates in double stranded DNA breaks, artificially induced by the rare-cleaving enzymes I-SceI or I-CeuI. The reports also included donor T-DNA vectors which comprised a recognition site for the respective rare-cleaving enzyme.

However, the methods in the prior art frequently rely on the reformation or generation through homology recombination of an intact selectable or screenable marker gene.

Therefore, there remains a need for methods which would allow targeted exchange of virtually any target DNA sequence by a replacement DNA. These and other problems are solved as described hereinafter in the different detailed embodiments of the invention, as well as in the claims.

SUMMARY OF THE INVENTION

In one embodiment of the invention a method is described for introduction of a DNA molecule of interest into the genome of a plant cell or plant followed by removal of a subsequence of the DNA molecule of interest, preferably comprising a selectable or screenable marker, comprising the steps of a. Introducing the DNA molecule of interest into the genome of the plant cell, the DNA molecule of interest comprising the subsequence of the DNA molecule flanked by two DNA sequences arranged in direct repeat and further comprising at least one recognition site for a rare cleaving double stranded DNA break inducing (DSBI) enzyme located in the vicinity of, preferably between, the two DNA sequences arranged in direct repeat;
b. Selecting a plant cell wherein the DNA molecule of interest is integrated in the genome and regenerating a plant from the plant cell;
c. Crossing the plant with a second plant comprising a DSBI enzyme encoding chimeric gene, the chimeric gene comprising the following operably linked DNA segments:
   i. a microspore specific promoter fragment, such as a promoter fragment selected from the nucleotide sequence of SEQ ID No. 3;
   ii. a DNA region encoding a rare cleaving double stranded DNA break inducing enzyme recognizing the recognition site, such as an endonuclease selected from the group of I-Sce I, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-DhaI, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I or PI-Tsp I or a chimeric endonuclease comprising a Zn finger DNA binding domain and a DNA cleavage domain;
   iii. a transcription termination and polyadenylation region;
d. Selecting a progeny plant (F1-plant) comprising the DNA molecule of interest and the DSBI enzyme encoding chimeric gene;
e. Crossing the progeny plant with another plant whereby the progeny plant is used as pollen donor;
f. Selecting a population of progeny plants (F2-population) which comprises the DSBI enzyme encoding chimeric gene; and
g. Selecting a progeny plant wherein subsequence of the DNA molecule has been deleted by homologous recombination between the two DNA sequences arranged in direct repeat and optionally
h. Crossing the progeny plant wherein the subsequence of the DNA molecule has been deleted, with another plant; and
i. Obtaining a population of progeny plants (F3-plants) and selecting plants which do not contain the rare cleaving DSBI enzyme encoding chimeric gene.

In another embodiment of the invention, a method is provided for exchanging a target DNA sequence in the genome, particularly the nuclear genome, of a plant for a DNA sequence of interest comprising the following steps:

a. Inducing a first double stranded DNA break at a preselected site in the genome of a cell of a plant, the preselected site being located within the target DNA sequence or in the vicinity of the target DNA sequence;
b. Introducing a DNA molecule of interest into the plant cell, the DNA molecule comprising
   i. The DNA sequence of interest located between two flanking DNA regions having at least 80% sequence homology, preferably 100% sequence homology to a DNA region flanking the target DNA sequence, and preferably flanking the preselected site in the genome of the plant cell;
   ii. A selectable or screenable marker gene located between the flanking DNA regions, the selectable or screenable marker gene further being located between one of the flanking DNA regions and a partial flanking DNA region, comprising part of the one of the flanking DNA regions, located in direct repeat;
   iii. A recognition site for a DSBI enzyme located between the one of the flanking DNA regions and the partial flanking DNA region located in direct repeat;
c. Selecting a population of plant cells comprising the selectable or screenable marker;
d. Selecting a plant cell wherein the DNA sequence of interest (and the selectable or screenable marker) has been introduced by homologous recombination through the flanking DNA regions, and regenerating a plant from the plant cell;
e. Crossing the regenerated plant or a progeny plant thereof comprising the selectable marker gene with a plant comprising a rare cleaving double stranded break inducing ("DSBI") enzyme encoding chimeric gene, the chimeric gene comprising the following operably linked DNA segments:
   i. a microspore specific promoter;
   ii. a DNA region encoding a double stranded DNA break inducing enzyme recognizing the recognition site located in the DNA of interest;
   iii. a transcription termination and polyadenylation region;
f. Selecting a progeny plant (F1-plant) comprising the selectable or screenable marker gene and the DSBI enzyme encoding chimeric gene;
g. Crossing the progeny plant with another plant whereby the progeny plant is used as pollen donor;
h. Selecting a population of progeny plants (F2-population) which comprises the DSBI enzyme encoding chimeric gene; and
i. Selecting a progeny plant wherein the selectable or screenable marker gene is deleted by homologous recombination between the one of the flanking DNA regions and a partial flanking DNA region comprising part of the one of the flanking DNA regions.

The invention relates to the plants obtainable by the above described methods

In yet another embodiment, the invention relates to a plant comprising a rare cleaving DSBI enzyme encoding chimeric gene, such as the chimeric gene of SEQ ID NO 6 from nucleotide 1941 to nucleotide 3913, the chimeric gene comprising the following operably linked DNA segments:

i. a microspore specific promoter such as a promoter fragment selected from the nucleotide sequence of SEQ ID No 3 or a functional fragment thereof;

ii. a DNA region encoding a double stranded DNA break inducing enzyme recognizing the recognition site located in the DNA of interest, such as an endonuclease selected from the group of I-Sce I, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-DhaI, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I or PI-Tsp I or a chimeric endonuclease comprising a Zn finger DNA binding domain and a DNA cleavage, particularly the DNA region comprising the nucleotide sequence of SEQ ID No 1 or SEQ ID No 2; and iii. a transcription termination and polyadenylation region.

The invention also relates to the chimeric gene described above.

In another embodiment of the invention, a DNA vector is provided for exchanging a target DNA sequence in the genome of a plant cell for a DNA sequence of interest through the induction of a double stranded break at a preselected site within the target sequence or in the vicinity thereof, the DNA vector comprising a. the DNA sequence of interest located between two flanking DNA regions having at least 80% sequence homology, preferably a 100% sequence homology to a DNA region flanking the target DNA sequence and flanking the preselected site;

b. a selectable or screenable marker gene located between the flanking DNA regions, the selectable or screenable marker gene further being located between one of the flanking DNA regions and a partial flanking DNA region comprising part of the one of the flanking DNA regions located in direct repeat; and c. a recognition site for a DSBI enzyme located between the one of the flanking DNA regions and the partial flanking DNA region located in direct repeat.

BRIEF DESCRIPTION OF THE DRAWINGS

FIG. 1 is schematic representation of a method for introducing a DNA of interest having a selected subpart comprising a selectable or screenable marker gene into a cell of a plant and subsequently removing the selected subpart of the DNA of interest. Trait: represents any DNA sequence of interest; DSB: recognition site for a double stranded break inducing enzyme ("DSBIE"); SMG1: selectable marker gene or screenable marker gene; drs: direct repeat sequence; SMG2: selectable or screenable marker gene associated with the DSBIE encoding chimeric gene; MSP: microspore specific promoter; 3': transcription termination and polyadenylation signal;

FIG. 2 is a schematic representation of a method allowing exact replacement of a target DNA sequence with a replacement DNA sequence. DSB1: recognition site for a first double stranded break inducing enzyme; FS1: flanking sequence 1; FS2: flanking sequence 2; DSB2: recognition site for a second double stranded break inducing enzyme; SMG1: selectable marker gene 1 or screenable marker gene 1; SMG2: selectable marker gene 2 or screenable marker gene 2; DSBIE: double stranded break inducing enzyme; dr1: direct repeat sequence 1 (which is similar or identical to the direct repeat sequence 2 that is part of flanking sequence 2; also indicated herein as "partial flanking DNA region"); MSP: microspore specific promoter; 3': transcription termination and polyadenylation signal.

FIG. 3 is a schematic representation of a method allowing exact replacement of a target DNA sequence with a replacement DNA sequence similar to the method illustrated in FIG. 2. dr1 in this case is a direct repeat sequence which is part from flanking sequence 1 and which is similar or identical to the direct repeat sequence 2 (dr2).

DETAILED EMBODIMENTS OF THE INVENTION

The current invention is based on the finding that selected sequences of a DNA molecule which are flanked by two direct repeats, and which are located in the neighborhood of a recognition site for a rare-cleaving double stranded DNA break inducing enzyme can be efficiently removed when the plant comprising such DNA is first crossed with a plant comprising a chimeric gene encoding the double stranded DNA break inducing rare-cleaving enzyme under control of a microspore-specific promoter, and pollen of a resulting plant is used to pollinate a receptor plant.

Figure 1A:
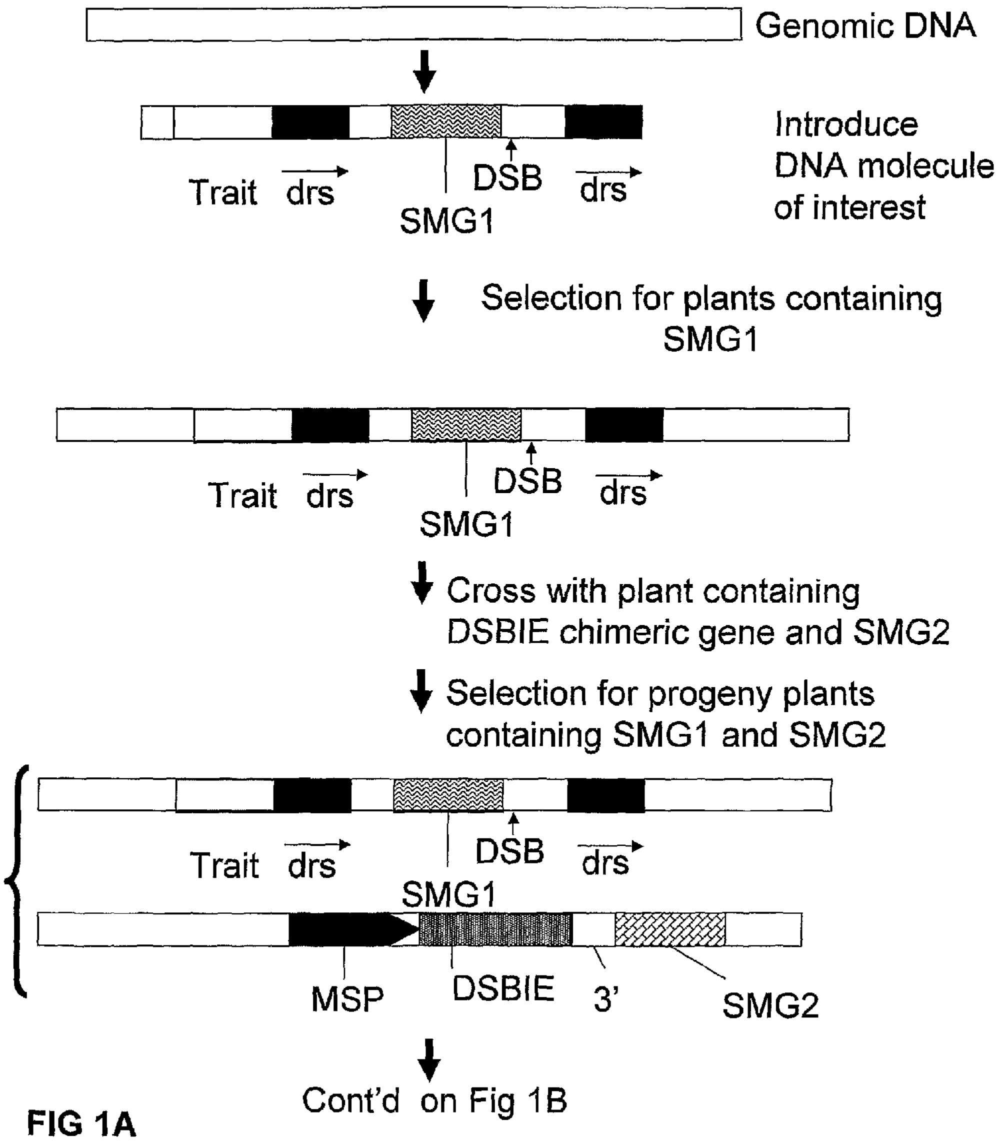
FIGS. 1 to 3 represent different embodiments of the method to remove a selected subpart of a DNA of interest which is or has been introduced into a cell of a plant. They are for illustration purposes only and should not be used to construe the claims in a limiting manner.
Figure 1B:
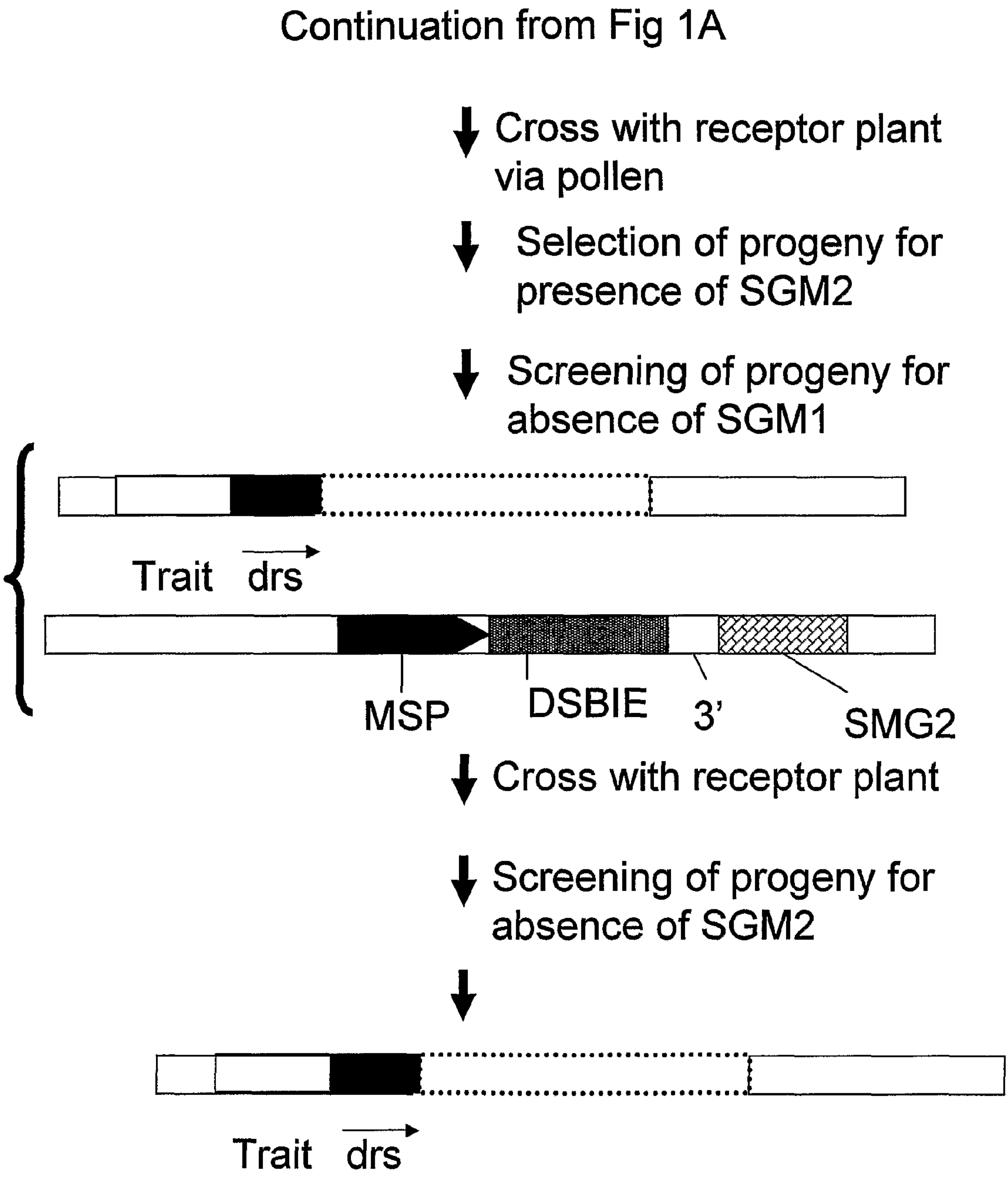

Thus, the invention is in one embodiment directed towards the use of plant comprising a chimeric gene encoding a double stranded DNA break inducing rare-cleaving endonuclease under control of a microspore specific promoter, to remove, by crossing, a DNA fragment located in the vicinity of a recognition site for the double stranded DNA break inducing rare-cleaving endonuclease and further located between two sequences located in direct repeat orientation (see FIG. 1). The expression of the rare cleaving DSBI endonuclease in the microspore during the pollen formation is sufficient to induce double stranded DNA breaks and thereby significantly stimulates the intrachromosomal homologous recombination between the directly repeated sequences, resulting in a removal of the sequences located between these directly repeated sequences.

In other words, in one embodiment of the invention, a method for introduction of a DNA molecule of interest into the genome of a plant cell or plant followed by removal of a subsequence of that DNA molecule is provided comprising the steps of a. Introducing that DNA molecule of interest into the genome of the plant cell comprising the subsequence of that DNA molecule flanked by two DNA sequences arranged in direct repeat and further comprising at least one recognition site for a double stranded DNA break inducing (DSBI) rare cleaving endonuclease located between the two DNA sequences arranged in direct repeat;

b. Selecting a plant cell wherein the DNA molecule of interest is integrated in the genome and regenerating a plant from the plant cell;

c. Crossing the plant with a second plant comprising a DSBI enzyme encoding chimeric gene, the chimeric gene comprising the following operably linked DNA segments:

i. a microspore specific promoter;

ii. a DNA region encoding a rare cleaving double stranded DNA break inducing enzyme recognizing the recognition site;

iii. a transcription termination and polyadenylation region;

d. Selecting a progeny plant (F1-plant) comprising the DNA molecule of interest and the DSBI enzyme encoding chimeric gene;

e. Crossing the progeny plant with another plant whereby the progeny plant is used as pollen donor;

f. Selecting a population of progeny plants (F2-population) which comprises the DSBI enzyme encoding chimeric gene; and g. Selecting a progeny plant wherein the subsequence of the DNA molecule of interest has been deleted by homologous recombination between the two DNA sequences arranged in direct repeat.

As used herein, a "double stranded DNA break inducing rare-cleaving endonuclease" is an enzyme capable of inducing a double stranded DNA break at a particular nucleotide sequence, called the "recognition site". Rare-cleaving endonucleases, also sometimes called mega-nucleases have a recognition site of 14 to 40 consecutive nucleotides. Therefore, rare-cleaving endonucleases have a very low frequency of cleaving, even in the larger plant genomes. Homing endonucleases constitute a family of such rare-cleaving endonucleases. They may be encoded by introns, independent genes or intervening sequences, and present striking structural and functional properties that distinguish them from the more classical restriction enzymes, usually from bacterial restriction-modification Type II systems. Their recognition sites have a general asymmetry which contrast to the characteristic dyad symmetry of most restriction enzyme recognition sites. Several homing endonucleases encoded by introns or inteins have been shown to promote the homing of their respective genetic elements into allelic intronless or inteinless sites. By making a site-specific double strand break in the intronless or inteinless alleles, these nucleases create recombinogenic ends, which engage in a gene conversion process that duplicates the coding sequence and leads to the insertion of an intron or an intervening sequence at the DNA level.

A well characterized homing endonuclease is I-SceI. I-SceI is a site-specific endonuclease, responsible for intron mobility in mitochondria in *Saccharomyces cerevisea*. The enzyme is encoded by the optional intron Sc LSU.1 of the 21S rRNA gene and initiates a double stranded DNA break at the intron insertion site generating a 4 bp staggered cut with 3'OH overhangs. The recognition site of I-SceI endonuclease extends over an 18 bp non-symmetrical sequence (Colleaux et al. 1988 *Proc. Natl. Acad. Sci. USA* 85: 6022-6026). The amino acid sequence for I-SceI and a universal code equivalent of the mitochondrial I-SceI gene have been provided by e.g. WO 96/14408. WO 96/14408 further discloses a number of variants of I-SceI protein which are still functional.

PCT application PCT/EP04/013122 (incorporated herein by reference) provides synthetic nucleotide sequence variants of I-SceI which have been optimized for expression in plants. The nucleotide sequence of such synthetic I-Sce I coding regions is set forth in SEQ ID No 1 in UIPAC code. The symbols of the UIPAC code have their usual meaning i.e. N=A or C or G or T; R=A or G; Y=C or T; B=C or G or T (not A); V=A or C or G (not T); D=A or G or T (not C); H=A or C or T (not G); K=G or T; M=A or C; S=G or C; W=A or T.

A list of other rare cleaving DSB inducing enzymes and their respective recognition sites is provided in Table I of WO 03/004659 (pages 17 to 20) (incorporated herein by reference). These include I-Sce I, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-DhaI, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I or PI-Tsp I.

Furthermore, methods are available to design custom-tailored rare-cleaving endonucleases that recognize basically any target nucleotide sequence of choice. Briefly, chimeric restriction enzymes can be prepared using hybrids between a zinc-finger domain designed to recognize a specific nucleotide sequence and the non-specific DNA-cleavage domain from a natural restriction enzyme, such as FokI. Such methods have been described e.g. in WO 03/080809, WO94/18313 or WO95/09233 and in Isalan et al., 2001, *Nature Biotechnology* 19, 656-660; Liu et al. 1997, *Proc. Natl. Acad. Sci.* USA 94, 5525-5530). Another way of producing custom-made meganucleases, by selection from a library of variants, is described in WO2004/067736.

As used herein "flanked by two DNA sequences arranged in direct repeat" indicates that the sequence to be removed from the introduced DNA molecule is immediately preceded and followed by two DNA regions, one at each end, wherein said two DNA regions are essentially similar in nucleotide sequence. The directly repeated sequences need not be identical, but may vary between about 75% to about 100% sequence identity. The shorter the repeated sequence, the more stringent the requirement for sequence similarity preferably is. However, in order to restore the DNA sequence without leaving a footprint, as described hereinafter, the DNA sequences arranged in direct repeat should preferably be identical. For avoidance of doubt, if the two DNA regions essentially similar in nucleotide sequence are contained within a double stranded DNA molecule, these DNA sequences are to be located on the same DNA strand, in the same 5'->3' direction.

The repeated DNA sequence may be at least 10, 50 or 100 nucleotides in length, but the sequence may of course be larger. It has however been found that repeats longer than 300 nucleotides do not any longer significantly enhance the intrachromosomal homology recombination resulting in the removal of the DNA sequence located between the direct repeat sequences.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970) Computer-assisted sequence alignment, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

Although the DSBI recognition site is preferably located between the directly repeated DNA sequences, this is not essential nor required. Indeed, the DSBI recognition site could also be part of one of the repeated DNA sequences.

As used herein "located in the vicinity" refers to the DSBI being located at a distance of between 500 bp, 1 kbp to 10 kbp from the directly repeated DNA sequences.

The methods herein described require the use of a chimeric gene encoding a rare-cleaving double stranded break inducing enzyme, whereby the coding region for the endonuclease is under control of a microspore specific promoter fragment.

As used herein "a microspore specific promoter region" or "a microspore specific promoter" or a "a microspore specific promoter fragment" is a promoter region or promoter or promoter fragment which can promote transcription selectively, preferably specifically, in the unicellular microspore of a plant. In angiosperm plants, sexual reproduction requires the production of viable male and female gametophytes. Pollen, as the male gametophyte if formed within the anther and is initiated from sporogenous cells, which develop into meiocytes. The meiocyte undergoes meiosis to form a tetrad of haploid microspores, which are subsequently released into the anther locule. Following expansion and vacuolation, an asymmetrical mitosis of the microspore results in bicellular pollen, containing a vegetative and a generative cell. In the majority of species, pollen is shed in bicellular condition. A suitable microspore specific promoter region is described in WO 97/30166 (incorporated herein by reference; see also SEQ ID No 3) as the promoter region from NTM19 gene in tobacco. A functional fragment thereof has been incorporated in the chimeric gene of the Examples (SEQ ID No 6). A microspore specific promoter fragment could include the nucleotide sequence of SEQ ID No 3 from position 1 to position 954 or from position 1 to position 993 or the nucleotide sequence of SEQ ID No 6 from position 1941 to 2926.

As used herein "coding region for a rare cleaving double stranded break inducing endonuclease" or "coding region for a rare cleaving double stranded break inducing enzyme" is a nucleotide sequence which encodes a polypeptide that is characterized as a rare cleaving DSBI enzyme such as the homing endonucleases or the chimeric endonucleases described elsewhere in this application. The coding region may thus comprise any nucleotide sequence that encodes any of the amino acid sequences of the homing endonucleases listed in the following table, which can be found in public databases under the mentioned accession numbers (all herein incorporated by reference):

| DSBI enzyme | Accession number |
|---|---|
| I-AniI | P03880 |
| I-CvuI | P56347 |
| I-CreI | P05725 |
| I-ChuI | Q32001 |
| I-CpaI - I-CpaIII - I-CpaIV - I-CpaV | Q39562/Q8WKZ5/Q8WKZ6/ Q8WKZ8 |
| I-CpaII | Q39559 |
| I-CeuI | P32761 |
| I-DmoI | P21505 |
| I-SceI | P03882 |
| I-SceII | P03878 |
| I-SceIII | Q9ZZX3 |
| PI-SceI | P17255 |
| I-NanI | Q25535 |
| I-NitI | Q25567 |
| I-NjaI | Q25568 |
| I-PpoI | Q94702 |
| PI-PfuI | O73954 |
| PI-PkoI | P77933 |
| PI-PkoII | P77933 |
| PI-PspI | Q51334 |
| PI-TfuI | P74918 |
| PI-TfuII | P74918 |
| PI-ThyI | Q9HH05 |
| PI-ThyII | Q9HH05 |
| PI-TliI | P30317 |
| PI-TliII | P30317 |
| I-TevI | P13299 |
| I-TevII | P07072 |
| I-TevIII | Q38419 |

It will be clear that for expression of the endonucleases under the control of a microspore specific promoter fragment, the coding region should be adapted so that the universal codon language is used to encode the above mentioned polypeptides. The coding region may further be optimized for expression in plants and the synthetic coding region have a nucleotide sequence which has been designed to fulfill the following criteria:

a) the nucleotide sequence encodes a functional rare cleaving double stranded break inducing endonuclease,
b) the nucleotide sequence has a GC content of about 50% to about 60%
c) the nucleotide sequence does not comprise a nucleotide sequence selected from the group consisting of GATAAT, TATAAA, AATATA, AATATT, GATAAA, AATGAA, AATAAG, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA;
d) the nucleotide does not comprise a nucleotide sequence selected from the group consisting of CCAAT, ATTGG, GCAAT and ATTGC;
e) the nucleotide sequence does not comprise a sequence selected from the group consisting of ATTTA, AAGGT, AGGTA, GGTA or GCAGG;
f) the nucleotide sequence does not comprise a GC stretch consisting of 7 consecutive nucleotides selected from the group of G or C;
g) the nucleotide sequence does not comprise a GC stretch consisting of 5 consecutive nucleotides selected from the group of A or T; and
h) the nucleotide sequence does not comprise codons coding for Leu, Ile, Val, Ser, Pro, Thr, Ala that comprise TA or CG duplets in positions 2 and 3 (i.e. the nucleotide sequence does not comprise the codons TTA, CTA, ATA, GTA, TCG, CCG, ACG and GCG).

The double stranded break inducing enzyme may comprise, but need not comprise, a nuclear localization signal (NLS) [Raikhel, *Plant Physiol.* 100: 1627-1632 (1992) and references therein], such as the NLS of SV40 large T-antigen [Kalderon et al. *Cell* 39: 499-509 (1984)]. The nuclear localization signal may be located anywhere in the protein, but is conveniently located at the N-terminal end of the protein. The nuclear localization signal may replace one or more of the amino acids of the double stranded break inducing enzyme.

Although the methods for removal are herein described as involving an active step of introduction of a DNA molecule of interest, followed by removal of selected subfragment thereof, it will be clear that the removal method of the invention can be used to remove any sequence located between direct DNA repeats, provided that a DSBI enzyme can be found or engineered that recognizes a DSBI recognition site in the vicinity of the repeated DNA sequences.

It will also be clear that the terms used to describe the method such as "introduction of a DNA fragment" as well as "regeneration of a plant from the cell" do not imply that such DNA fragment necessarily needs to be introduced by transformation techniques. Indeed, it will be immediately clear to the person skilled in the art that the DNA molecule of interest may also be introduced by breeding or crossing techniques from one plant to another.

However, it will be clear that the DNA molecule of interest may be introduced into the plant cells by any method known in the art, including *Agrobacterium* mediated transformation but also by direct DNA transfer methods. The transforming DNA molecule can be transferred into plant cells using any conventional method, including but not limited to direct DNA transfer method. As used herein "direct DNA transfer" is any method of DNA introduction into plant cells which does not involve the use of natural *Agrobacterium* spp. and which is capable of introducing DNA into plant cells. This includes methods well known in the art such as introduction of DNA by electroporation into protoplasts, introduction of DNA by electroporation into intact plant cells or partially degraded tissues or plant cells, introduction of DNA through the action of agents such as PEG and the like, into protoplasts, use of silicon whiskers, and bombardment with DNA coated microprojectiles.

The DNA may be integrated by homologous recombination or non-homologous end-joining methods involving a double stranded break induction at a preselected site as described e.g. in PCT/EP04/013122.

Figure 2A:
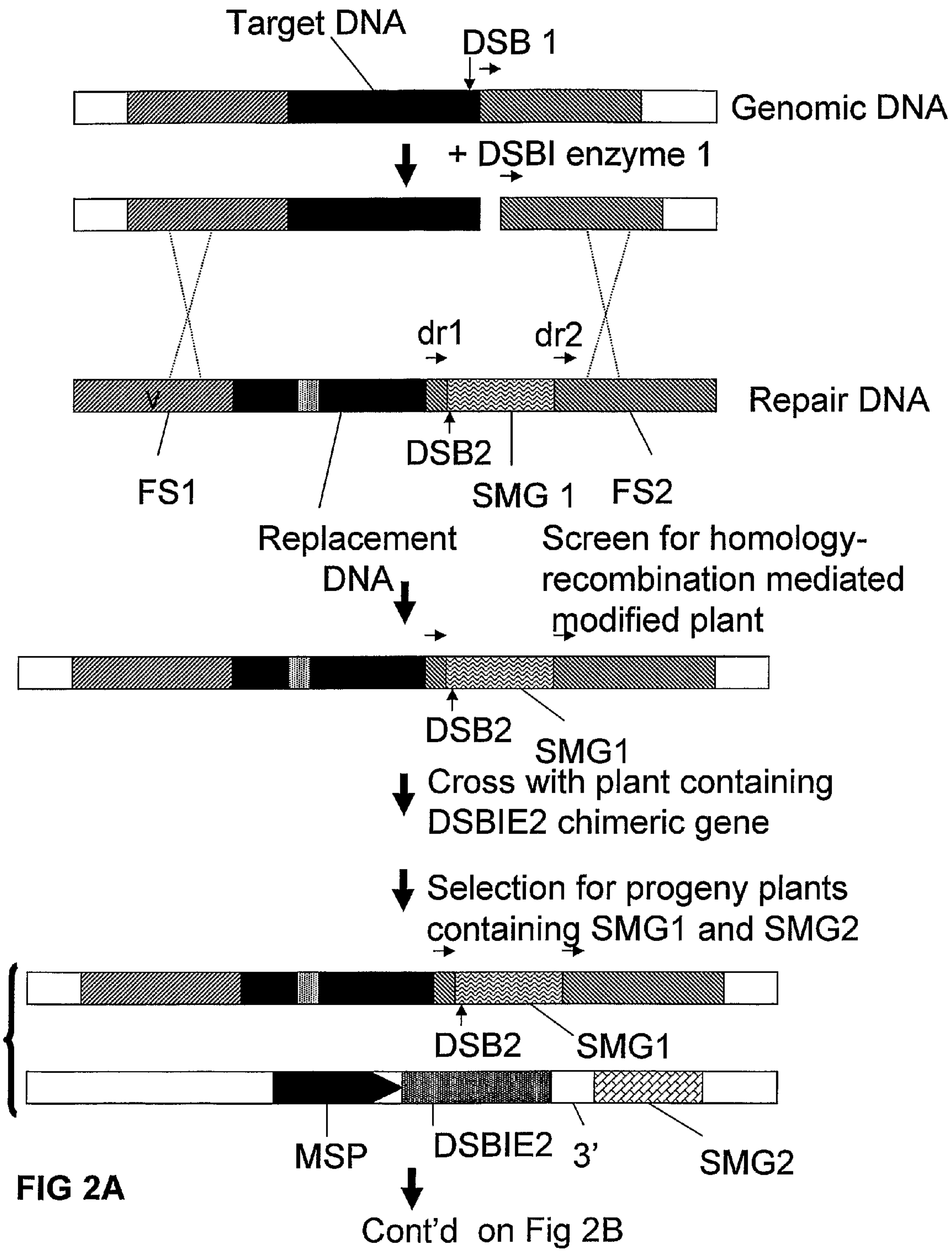
Figure 2B:
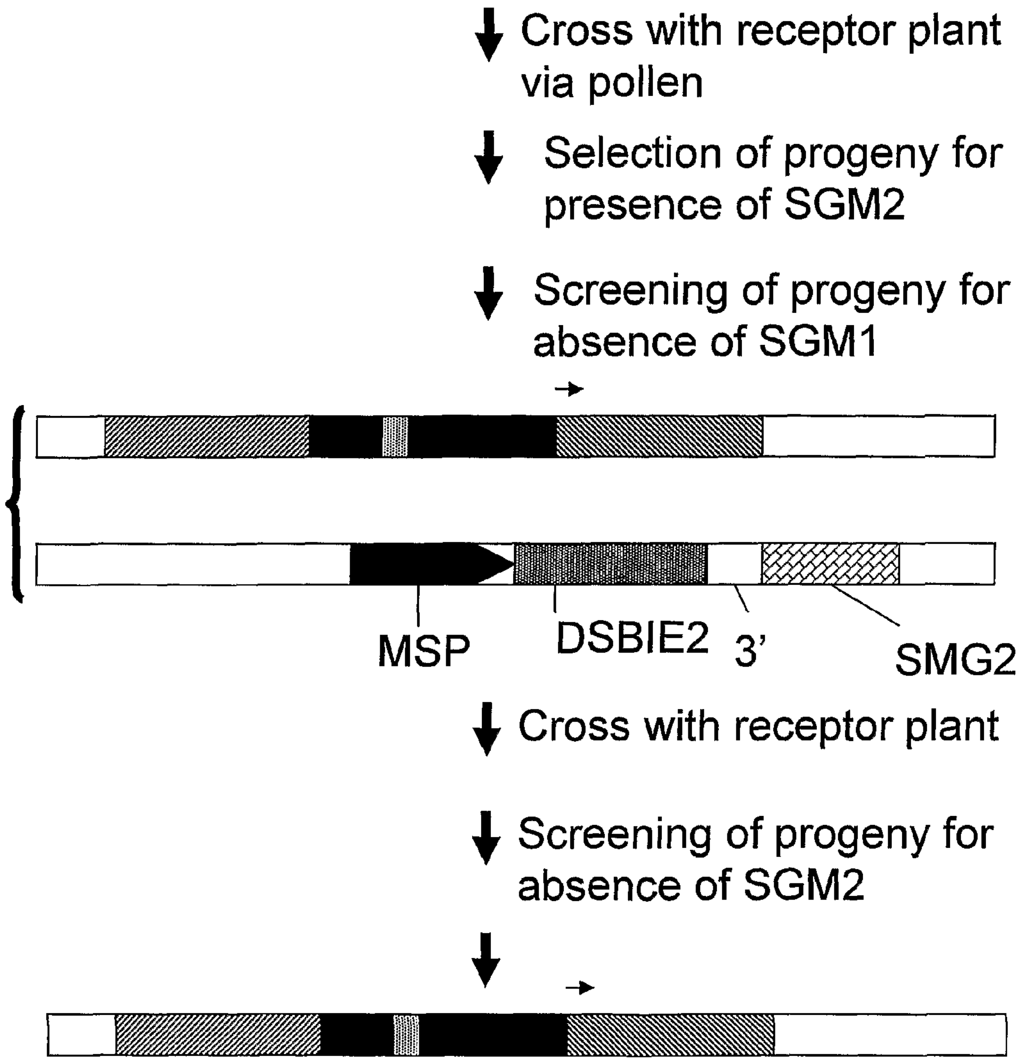
Figure 3A:
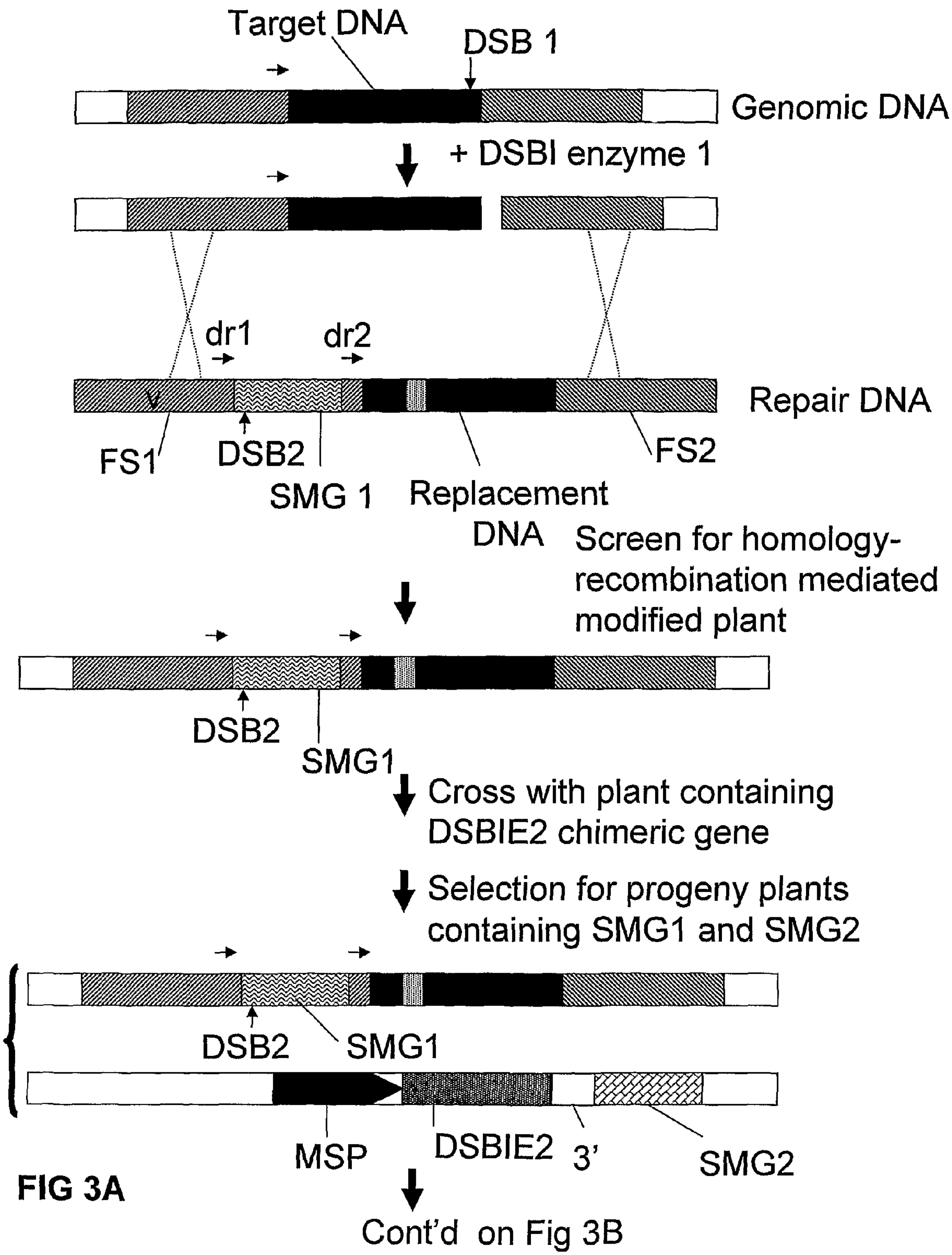
Figure 3B:
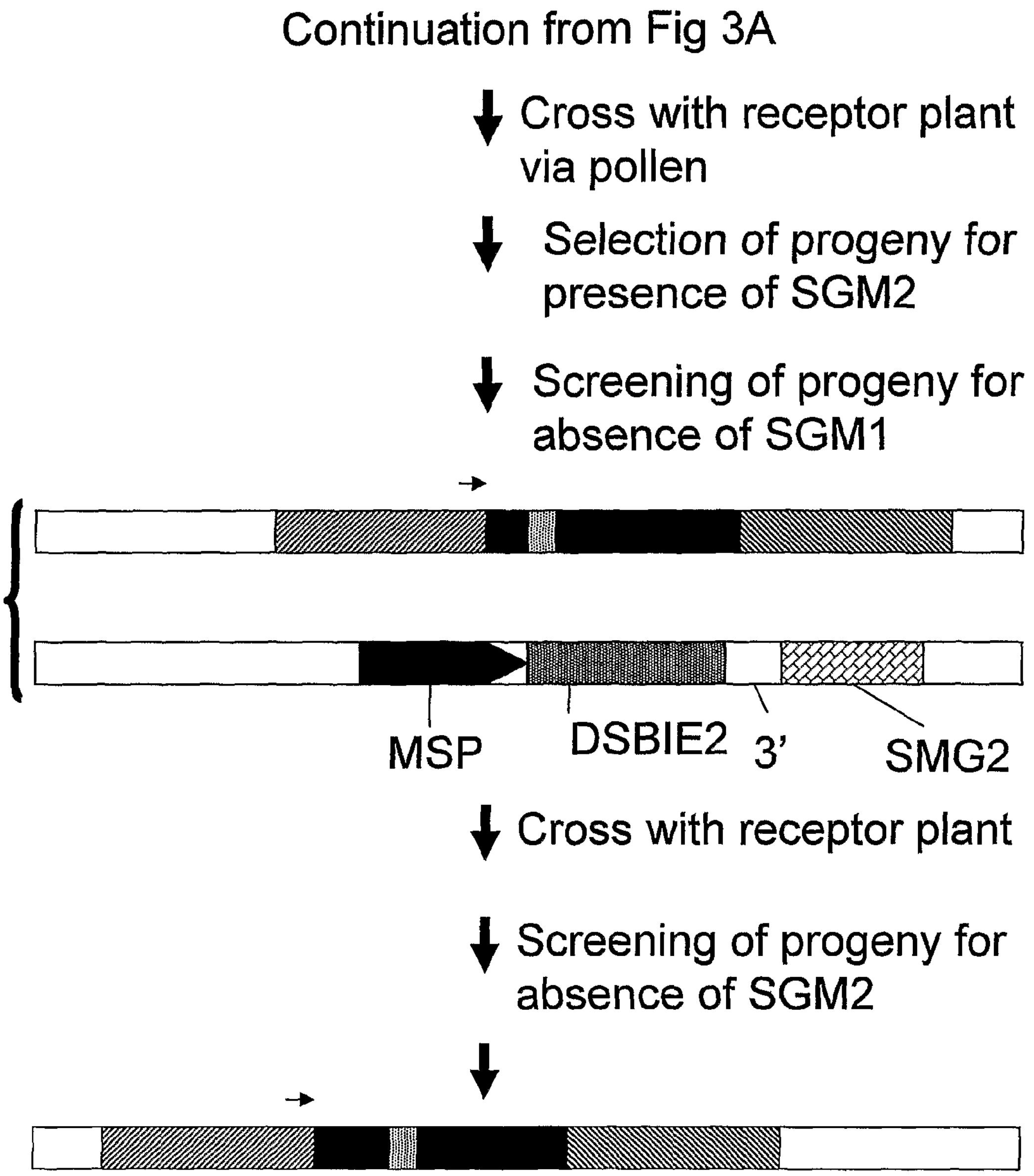

In one particular embodiment of the invention, the method of removal may be used in combination with DNA insertion, deletion or replacement by targeted homologous recombination, and wherein the targeted DNA insertion is achieved using a selectable or screenable marker, followed by verification in the population of plant cells or plants comprising the selectable or screenable marker of those plant cells or plants wherein the targeted DNA insertion occurred by homologous recombination. When the flanking sequences and direct repeats are appropriately chosen, this method results in exact replacement of the target DNA for a DNA of interest, without any remainder ("footprint") of the DNA molecule of interest used to achieve the replacement. The method of removal further does not need any additional in vitro culture, thereby avoiding that somaclonal variations are generated. An schematical outline of the method can be found in FIGS. 2 and 3.

Interestingly, it has been observed that using the methods as described in PCT/EP04/013122 for targeted insertion of foreign DNA of interest through homologous recombination, those transformation events wherein the foreign DNA is indeed inserted through homologous recombination represent a relatively high proportion (in the order of 1 to 5%) of the total population of events wherein the DNA is incorporated in the plant chromosome by any means. Accordingly, there is no need to rely on the generation or recreation through the homologous recombination of a DNA sequence resulting in a recognizable phenotype (such as the creation of an intact selectable marker gene after homologous recombination) to identify those events whereby the DNA is inserted by homologous recombination. Rather, a selectable or screenable marker gene can be included in the DNA region between the flanking DNA sequences followed by analysis of a relatively small number of transformed plant cells or plants, for identification of those transformation events wherein targeted DNA insertion occurred through homologous recombination.

Thus, in this embodiment of the invention, a method is provided for exchanging a target DNA sequence in cells of a plant for a DNA sequence of interest (or a foreign DNA) comprising the following steps:

- Inducing a first double stranded DNA break at a preselected site in the genome of the cell, the preselected site being located within the target DNA sequence or in the vicinity of said target DNA sequence;
- Introducing a DNA molecule of interest (of foreign DNA) into the plant cell, whereby the DNA molecule comprises the following operably linked DNA fragments:
  - i. a DNA molecule of interest located between two flanking DNA regions having at least 80% sequence homology, preferably 100% sequence homology to a DNA region flanking the target DNA sequence and flanking the preselected site in the genome of the plant cell;
  - ii. A selectable or screenable marker gene located between the flanking DNA regions, whereby the selectable or screenable marker gene is further located between one of the flanking DNA regions and another copy of at least part of the mentioned one of the flanking DNA regions located in direct repeat (also indicated as partial flanking DNA sequence);
  - iii. A recognition site for a DSBI enzyme located between the one of the flanking DNA regions and the partial flanking DNA region located in direct repeat;
- Selecting a population of plant cells comprising the selectable or screenable marker;
- Selecting a plant cell wherein the selectable or screenable marker has been introduced by homologous recombination through the flanking DNA regions and regenerating a plant from the plant cell;
- Crossing the regenerated plant or a progeny plant thereof comprising the selectable marker gene with a plant comprising a DSBI enzyme encoding chimeric gene, the chimeric gene comprising the following operably linked DNA segments:
  - a microspore specific promoter;
  - a DNA region encoding a double stranded DNA break inducing enzyme recognizing the recognition site located in the DNA of interest;
  - a transcription termination and polyadenylation region;
- Selecting a progeny plant (F1-plant) comprising the selectable or screenable marker gene and the DSBI enzyme encoding chimeric gene;
- Crossing the progeny plant with another plant whereby the progeny plant is used as pollen donor;
- Selecting a population of progeny plants (F2-population) which comprises the DSBI enzyme encoding chimeric gene; and
- Selecting a progeny plant within said F2 population wherein the selectable or screenable marker gene is deleted by homologous recombination between the one of the flanking DNA regions and a partial flanking DNA region comprising part of the one of the flanking DNA regions.

Thus, as used herein "a preselected site" indicates a particular nucleotide sequence in the plant nuclear genome, located in or near the target DNA sequence at which location it is desired to insert the foreign DNA or to exchange the target DNA sequence. A person skilled in the art would be able to either choose a double stranded DNA break inducing ("DSBI") enzyme recognizing the selected target nucleotide sequence or engineer such a DSBI endonuclease. Alternatively, a DSBI endonuclease recognition site may be introduced into the plant genome using any conventional transformation method or by conventional breeding using a plant line having a DSBI endonuclease recognition site in its genome, and any desired foreign DNA may afterwards be introduced into that previously introduced preselected target site.

The double stranded DNA breaks in the transforming DNA molecule may be induced conveniently by transient introduction of a plant-expressible chimeric gene comprising a plant-expressible promoter region operably linked to a DNA region encoding a double stranded break inducing enzyme. The DNA region encoding a double stranded break inducing enzyme may be a synthetic DNA region, such as but not limited to, a synthetic DNA region whereby the codons are chosen according to the design scheme as described elsewhere in this application for I-SceI encoding regions. The endonuclease itself, as a protein, could also be introduced into the plant cells, e.g. by electroporation. However, the endonuclease can also be provided in a transient manner by introducing into the genome of a plant cell or plant, a chimeric gene comprising the endonuclease coding region operably linked to an inducible plant-expressible promoter, and providing the appropriate inducible compound for a limited time prior to, during or immediately after introduction of the transforming DNA molecule. The endonuclease could also be provided as an RNA precursor encoding the endonuclease.

The double stranded break inducing enzyme may comprise, but need not comprise, a nuclear localization signal (NLS) [Raikhel, *Plant Physiol.* 100: 1627-1632 (1992) and references therein], such as the NLS of SV40 large T-antigen [Kalderon et al. *Cell* 39: 499-509 (1984)]. The nuclear localization signal may be located anywhere in the protein, but is conveniently located at the N-terminal end of the protein. The nuclear localization signal may replace one or more of the amino acids of the double stranded break inducing enzyme.

As used herein, the "target DNA sequence" is the DNA sequence located in the genome of the plant cell which is modified, by addition, deletion or substitution.

As used herein "flanking DNA regions" are DNA sequences having homology to the DNA regions respectively upstream or downstream of the target DNA sequence. This allows to better control the insertion of the foreign DNA or the DNA molecule of interest. Indeed, integration by homologous recombination will allow precise joining of the foreign DNA fragment to the plant nuclear genome up to the nucleotide level.

The flanking DNA regions may vary in length, and should be at least about 10 nucleotides in length. However, the flanking region may be as long as is practically possible (e.g. up to about 100-150 kb such as complete bacterial artificial chromosomes (BACs)). Preferably, the flanking region will be about 50 bp to about 2000 bp. Moreover, the regions flanking the foreign DNA of interest need not be identical to the DNA regions flanking the preselected site and may have between about 80% to about 100% sequence identity, preferably about 95% to about 100% sequence identity with the DNA regions flanking the preselected site. The longer the flanking region, the less stringent the requirement for homology. Furthermore, it is preferred that the sequence identity is as high as practically possible in the vicinity of the location of exact insertion of the foreign DNA. Furthermore, to achieve exchange of the target DNA sequence without changing the DNA sequence of the adjacent DNA sequences, the flanking DNA sequences should preferably be identical to the DNA regions flanking the preselected site.

Moreover, the regions flanking the foreign DNA of interest need not have homology to the regions immediately flanking the preselected site, but may have homology to a DNA region of the nuclear genome further remote from that preselected site. Insertion of the foreign DNA will then result in a removal of the target DNA between the preselected insertion site and the DNA region of homology. In other words, the target DNA located between the homology regions will be substituted for the foreign DNA of interest.

Preferably, the preselected site and the further mentioned recognition sequence are recognized by different rare cleaving double stranded break inducing endonucleases.

The mentioned "partial flanking DNA region" indicates that the DNA region comprises at least a portion of the flanking DNA region adjacent to DNA region to be deleted and which usually will comprise the selectable or screenable marker. It is clear that the partial flanking DNA sequence may also be equal in length to the flanking DNA sequence or even comprise a longer flanking DNA sequence.

"Selectable or screenable markers" as used herein have there usual meaning in the art and include, but are not limited to plant expressible phosphinotricin acetyltransferase, neomycine phosphotransferase, glyphosate oxidase, glyphosate tolerant EPSP enzyme, nitrilase gene, mutant acetolactate synthase or acetohydroxyacid synthase gene, β-glucoronidase (GUS), R-locus genes, green fluorescent protein and the likes.

The selection of the plant cell or plant wherein the selectable or screenable marker and the rest of the foreign DNA molecule has been introduced by homologous recombination through the flanking DNA regions can e.g. be achieved by screening for the absence of sequences present in the transforming DNA but located outside of the flanking DNA regions. Indeed, presence of sequences from the transforming DNA outside the flanking DNA regions would indicate that the transformed plant cells origination by random DNA insertion. To this end, selectable or screenable markers may be included in the transforming DNA molecule outside of the flanking DNA regions, which can then be used to identify those plant cells which do not have the selectable or screenable markers located outside of the transforming DNA and which may have arisen by homologous recombination through the flanking DNA regions. Alternatively, the transforming DNA molecule may contain selectable markers outside the flanking DNA regions that allow selection for the absence of such genes (negative selectable marker genes).

In another embodiment of the invention, the DNA removal method described herein may be combined with a method for DNA insertion at a preselected site in the genome of a cell, based on non-homologous end-joining.

Accordingly, the invention provides a method for inserting a selected DNA molecule at a predetermined location in the genome, preferably the nuclear genome of a plant cell, comprising the following steps:

- Inducing a first double stranded DNA break at a preselected site in the genome of the cell, the preselected site preferably being located within a target DNA sequence;
- Introducing a foreign DNA molecule into the plant cell, whereby the DNA molecule comprises the following operably linked DNA fragments:
  - the selected DNA molecule of interest;
  - A selectable or screenable marker gene preceded or followed by a repeat DNA region having at least 80% sequence identity to one of the genomic DNA regions located adjacent to the preselected site whereby the DNA region is located in direct repeat with the genomic copy thereof upon insertion of the foreign DNA molecule in the preselected site by non-homologous end joining;
  - A recognition site for a rare cleaving DSBI enzyme located in the region of the foreign DNA comprising said repeat DNA region and said selectable marker gene;
- Selecting a population of plant cells comprising the selectable or screenable marker;
- Selecting a plant cell wherein the selectable or screenable marker has been introduced by non homologous end-joining at the preselected site and regenerating a plant from the plant cell;
- Crossing the regenerated plant or a progeny plant thereof comprising the selectable marker gene with a plant comprising a DSBI enzyme encoding chimeric gene, the chimeric gene comprising the following operably linked DNA segments:
  - a microspore specific promoter;
  - a DNA region encoding a double stranded DNA break inducing enzyme recognizing the recognition site located in the DNA of interest;

a transcription termination and polyadenylation region;

Selecting a progeny plant (F1-plant) comprising the selectable or screenable marker gene and the DSBI enzyme encoding chimeric gene;

Crossing the progeny plant with another plant whereby the progeny plant is used as pollen donor;

Selecting a population of progeny plants (F2-population) which comprises the DSBI enzyme encoding chimeric gene; and Selecting a progeny plant within said F2 population wherein the selectable or screenable marker gene is deleted by homologous recombination between the repeat DNA region and the genomic DNA regions located adjacent to the preselected site.

The above mentioned method can be conveniently used to interrupt any DNA sequence of choice, such as e.g. a polypeptide coding region, a biologically active RNA encoding DNA sequence, a promoter region, a regulatory region, a recognition site for protein or RNA binding etc.

In this embodiment, events wherein the DNA molecule has been inserted by non-homologous end-joining can be conveniently identified by e.g. a PCR reaction using a primer sequence recognizing a genomic sequence located in the vicinity of the preselected site, and which further preferably does not recognize the foreign DNA, and a primer within the foreign DNA molecule. Upon insertion of the foreign DNA by non-homologous end-joining at the preselected a DNA fragment will be amplified. Such DNA fragment would not be amplified when a the foreign DNA is randomly integrated.

It will be appreciated that the means and methods of the invention may be used in any plant capable of reproduction through pollen, including corn, tobacco, cereal plants including wheat, oat, barley, rye, rice, turfgrass, sorghum, millet or sugarcane plants. The methods of the invention can also be applied to any plant (Angiospermae or Gymnospermae) including but not limited to cotton, canola, oilseed rape, soybean, vegetables, potatoes, Lenma spp., Nicotiana spp., Arabidopsis, alfalfa, barley, bean, corn, cotton, flax, pea, rape, rice, rye, safflower, sorghum, soybean, sunflower, tobacco, wheat, asparagus, beet, broccoli, cabbage, carrot, cauliflower, celery, cucumber, eggplant, lettuce, onion, oilseed rape, pepper, potato, pumpkin, radish, spinach, squash, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut and watermelon.

It is also an object of the invention to provide plant cells and plants generated according to the methods of the invention. Gametes, seeds, embryos, either zygotic or somatic, progeny or hybrids of plants comprising the DNA insertion events, which are produced by traditional breeding methods are also included within the scope of the present invention. Such plants may contain a heterologous DNA sequence instead of a target sequence, and will only be different from their progenitor plants by the presence of this heterologous DNA or DNA sequence post exchange.

The plants obtained by the methods described herein may be further crossed by traditional breeding techniques with other plants to obtain progeny plants comprising the targeted DNA insertion events obtained according to the present invention.

The following non-limiting Examples describe the removal of a selected subfragment from an introduced DNA molecule using a double strand DNA break inducing enzyme, such as I-SceI, expressed under control of a microspore specific promoter encoding chimeric gene.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Throughout the description and Examples, reference is made to the following sequences:

SEQ ID No 1: nucleotide sequence of synthetic I-SceI coding region (UIPAC code).

SEQ ID No 2: nucleotide sequence of synthetic I-SceI coding region.

SEQ ID No 3: nucleotide sequence of microspore selective NTM19 gene including promoter region SEQ ID No 4: nucleotide sequence of the T-DNA of pTCV63

SEQ ID No 5: nucleotide sequence of the T-DNA of pTCV64

SEQ ID No 6: nucleotide sequence of the T-DNA of pTCV72

EXAMPLES

Removal of a Selectable Marker Gene by Intrachromosomal Homologous Recombination (IHR)

A recombination assay to detect removal of a selected DNA fragment has been developed based on the restoration of an egfp-bar fusion gene after removal of a selectable marker gene (hyg) (~2000 bp) by intrachromosomal homologous recombination (IHR) between directly repeated sequences (part of egfp sequences; either about 300 bp or about 600 bp). One of the repeat sequences is flanked by an I-SceI (and Zinc finger Zif268) recognition site giving the possibility to create a DSB between the repeats. In order to allow the IHR during transition from one generation to another, the I-SceI endonuclease was placed under control of a microspore specific promoter (pNTM19).

Using standard recombinant DNA techniques, the following DNA molecules were constructed for use in the following experiments:

1. pTCV63: with short direct repeat sequences (~300 bp) containing the following operably linked DNA constructs:
   p35S3: a CaMV35S promoter fragment
   egf(short): a first part the eGFP coding sequence comprising a 300 bp overlap with the subsequently named GFP sequence
   a recognition site for I-SceI endonuclease
   a recognition site for Zif268 Zn finger containing DNA binding protein pCsVMV: a cassava vein mosaic virus promoter fragment hyg: coding region for hygromycin resistance 3'35S: 3' transcription termination and polyadenylation signal gfp(short): the 3' part of the eGFP coding sequence, comprising a direct repeat of 300 bp sequences of the previous egf portion of this plasmid, and wherein the coding region is translationally linked to a bar gene coding region 3'nos: a 3' transcription termination and polyadenylation signal from the nopaline synthase gene.

This plasmid was introduced into *Agrobacterium tumefaciens* and the resulting strain (A4330) was used to generate transgenic tobacco plants (G7NT001).

2. pTCV64: with long direct repeat sequences (~600 bp) containing the following operably linked DNA constructs:

p35S3: a CaMV35S promoter egf(long): a first part the eGFP coding sequence comprising a 600 bp overlap with the subsequently named gfp sequence a recognition site for I-SceI endonuclease a recognition site for Zif268 Zn finger containing DNA binding protein pCsVMV: a cassava vein mosaic virus promoter hyg: coding region for hygromycin resistance 3'35S: 3' transcription termination and polyadenylation signal gfp(long): the 3' part of the efgp coding sequence, comprising a direct repeat of 600 bp sequences of the previous egf construct, and wherein the coding region is translationally linked to a bar gene coding region 3'nos: a 3' transcription termination and polyadenylation signal from the nopaline synthase gene This plasmid was introduced into *Agrobacterium tumefaciens* and the resulting strain (A4364) was used to generate transgenic tobacco plants (G7NT004)

3. pTCV72:

pnos: a nopaline synthase promoter neo: neomycine phosphotransferase II coding region 3'ocs: a 3' transcription termination and polyadenylation signal from the octopine synthase gene;

pNTM19: a microspore specific promoter fragment

I-SceI: coding region for the endonuclease I-SceI

3'nos: a 3' transcription termination and polyadenylation signal from the CaMV 35S transcript This plasmid was introduced into *Agrobacterium tumefaciens* and the resulting strain (A4331) was used to generate transgenic tobacco plants (G7NT005)

From three independent single copy transformed tobacco lines of each G7NT001 and G7NT004 crosses have been made with two independent single copy transformed lines comprising the chimeric gene encoding I-SceI under control of a microspore specific promoter (G7NT005) using G7NT005 as male plant whereby the progeny lines were indicated as follows:

G7NT001-0001×G7NT005-0001>04TDNT000001
G7NT001-0002×G7NT005-0001>04TDNT000002
G7NT001-0003×G7NT005-0001>04TDNT000003
G7NT001-0001×G7NT005-0002>04TDNT000004
G7NT001-0002×G7NT005-0002>04TDNT000005
G7NT001-0003×G7NT005-0002>04TDNT000006
G7NT004-0001×G7NT005-0001>04TDNT000007
G7NT004-0002×G7NT005-0001>(no progeny)
G7NT004-0003×G7NT005-0001>04TDNT000012
G7NT004-0001×G7NT005-0002>04TDNT000008
G7NT004-0002×G7NT005-0002>04TDNT000010
G7NT004-0003×G7NT005-0002>04TDNT000011

From each crossing 200 seeds have been sown on Km (200 mg/L), 200 seeds on Hyg (50 mg/L) and 200 seeds on Km(200 mg/L)+Hyg(50 mg/L) to check normal transmission of transgenes. There was a quite normal transmission of the different transgenes for most of the crossings (note that for some crossings contamination problems and seed quality problems were encounter (see following table):

| | N° of seedlings resistant to the respective selective agent | | | |
|---|---|---|---|---|
| Line | n° seedlings/ 50 seeds | n° $Km^R$ seedlings/ 200 seeds | n° $Hyg^R$ seedlings/ 200 seeds | n° $Km^R$ + $Hyg^R$ seedlings/ 200 seeds |
| G7NT001-0001x G7NT005-0001 | 32 | 47/150 | 55 | 28/150 |
| G7NT001-0001x G7NT005-0002 | 32 | 29 | 51 | 15 |
| G7NT001-0002x G7NT005-0001 | 32 | 89 | 64 | 59 |
| G7NT001-0002x G7NT005-0002 | 46 | 69 | 94 | 42 |
| G7NT001-0003x G7NT005-0001 | 47 | 92 | 93 | 53 |
| G7NT001-0003x G7NT005-0002 | 48 | 88 | 85 | 47 |
| G7NT004-0001x G7NT005-0001 | 49 | 92 | 65/150 | 44 |
| G7NT004-0002x G7NT005-0001 | 47 | 73/150 | 89 | 34/150 |
| G7NT004-0002x G7NT005-0002 | 49 | 58/150 | 98 | 60 |
| G7NT004-0003x G7NT005-0001 | 39 | 63 | 69 | 50 |
| G7NT004-0003x G7NT005-0002 | 45 | 60 | 91 | 22 |

From each of these 12 crossings, a few $Km^R$+$Hyg^R$ progeny plants have been transferred to the greenhouse for being used as pollinator of WT SR1 plants. From these 12 crossings each time three $Km^R$+$Hyg^R$ plants have been used as pollinator of WT SR1 plants according to the following scheme:

SR1 × 04TDNT000001-001
-002
-003
SR1 × 04TDNT000002-001
-002
-003
SR1 × 04TDNT000003-001
-002
-003
SR1 × 04TDNT000004-001
-002
-003
SR1 × 04TDNT000005-001
-002
-003

-continued $SR1 \times 04TDNT000006$-001

-002

-003

$SR1 \times 04TDNT000007$-001

-002

-003

$SR1 \times 04TDNT0000012$-001

-002

-003

$SR1 \times 04TDNT000008$-001

-002

-003

$SR1 \times 04TDNT0000010$-001

-002

-003

-continued $SR1 \times 04TDNT0000011$-001

-002

-003

From each progeny of these crosses (see following tables) 50 seeds have been sown on non-selective substrate to determine the germination frequency, 50 seeds on kanamycin to determine the transmission rate of the NTM19-I-SceI gene and about 4000 seeds on PPT for determining the frequency of IHR during transition from one generation to the other. The number of $PPT^R$ seedlings which are also $Km^R$ determines whether or not there is an effect of DSB induction by NTM19-ISceI endonuclease on the frequency of IHR during transition from one generation to the other.

The results of the progeny analysis of 22 progenies are summarized in tables A, B and C.

There is a very strong effect of NTM19-I-SceI on the frequency of IHR during transition from one generation to another as all $PPT^R$ seedlings are also $Km^R$!

It has to be remarked that a large part of the $PPT^R$ and $GFP^F$ seedlings did not develop further into plants and died off due to the toxic effect of GFP.

TABLE A

| Cross | Germination frequency (n° seedlings/50 seeds) | N° $Km^R$ seedlings/50 seeds | N° $PPT^R$ and $GFP^F$ seedlings/n° of seeds | N° $Km^R$ seedlings/ N° of $PPT^R$ and $GFP^F$ seedlings screened for $km^R$ |
|---|---|---|---|---|
| SR1x04TDNT000001-001 short repeat | 43 | 24 | 77/4348 (1.77%) | 5/5 |
| SR1x04TDNT000001-002 short repeat | 49 | 20 | 79/4835 (1.63%) | 23/23 |
| SR1x04TDNT000001-003 short repeat | 47 | 22 | 98/4827 (2.03%) | 27/27 |
| SR1x04TDNT000002-001 short repeat | 47 | 23 | 33/4762 (0.69%) | 4/4 |
| SR1x04TDNT000004-001 short repeat | 49 | 30 | 123/4798 (2.6%) | 36/36 |
| SR1x04TDNT000004-002 short repeat | 48 | 23 | 100/4745 (2.1%) | 32/32 |
| SR1x04TDNT000004-003 short repeat | 48 | 15 | 118/4665 (2.5%) | 6/6 |
| SR1x04TDNT000005-001 short repeat | 49 | 25 | 94/4665 (2.01%) | 16/16 |
| SR1x04TDNT000005-002 short repeat | 48 | 20 | 47/4690 (1%) | 7/7 |
| SR1x04TDNT000005-003 short repeat | 48 | 22 | 120/4658 (2.6%) | 16/18 (2 S or R?) |
| SR1x04TDNT000006-001 short repeat | 47 | 28 | 136/4665 (2.9%) | 24/24 |
| SR1x04TDNT000006-003 short repeat | 49 | 20 | 77/4650 (1.66%) | 12/12 |

TABLE B

| Cross | Germination frequency (n° seedlings/ 50 seeds)* | N° $Km^R$ seedlings/ 50 seeds | N° $Hyg^R$ seedlings/ 50 seeds | N° of $Km^R$ + $Hyg^R$/ 100 seeds | N° $PPT^R$ and $GFP^F$ seedlings/N° of seeds** | N° $Km^R$ seedlings/ N° of $PPT^R$ and $GFP^F$ seedlings screened for $Km^R$ |
|---|---|---|---|---|---|---|
| SR1x04TDNT000003-001 short repeat | 23 | 14 | 12 | 13 | 44/4973 (0.89%)** | 33/33 |
| SR1x04TDNT000003-003 short repeat | 20 | 16 | 11 | 16 | 46/4857 (0.95%)** | 46/46 |

TABLE B-continued

| Cross | Germination frequency (n° seedlings/ 50 seeds)* | N° $Km^R$ seedlings/ 50 seeds | N° $Hyg^R$ seedlings/ 50 seeds | N° of $Km^R$ + $Hyg^R$/ 100 seeds | N° $PPT^R$ and $GFP^F$ seedlings/N° of seeds** | N° $Km^R$ seedlings/ N° of $PPT^R$ and $GFP^F$ seedlings screened for $Km^R$ |
|---|---|---|---|---|---|---|
| SR1x04TDNT000007-001 long repeat | 19 | 7 | 7 | 7 | 16/4915 (0.33%)** | 16/16 |
| SR1x04TDNT000008-001 long repeat | 28 | 17 | 12 | 12 | 33/4890 (0.7%)** | 33/33 |
| SR1x04TDNT000008-003 long repeat | 20 | 7 | 8 | 8 | 33/4840 (0.69%)** | 33/33 |
| SR1x04TDNT000012-003 long repeat | 16 | 10 | 9 | 9 | 14/4312 (0.32%)** | 14/14 |

*the progenies mentioned in this table were sown at the same moment. Due to a too drastic sterilization with bleach, there was a bad and irregular germination (for most lines <50%).

**This means that the N° of $PPT^R$ and $GFP^F$ seedlings/N° of seeds is an underestimation with at least a factor 2 as the germination frequency is for most lines less than 50%

TABLE C

| Cross | Germination frequency (n° seedlings/ 50 seeds)* | N° $Km^R$ seedlings/ 50 seeds | N° $Hyg^R$ seedlings/ 50 seeds | N° of $Km^R$ + $Hyg^R$/ 100 seeds | N° $PPT^R$ and $GFP^F$ seedlings/n° of seeds** | N° $Km^R$ seedlings/ N° of $PPT^R$ and $GFP^F$ seedlings screened for $Km^R$* |
|---|---|---|---|---|---|---|
| SR1x04TDNT000002-002 short repeat | 50 | 20 | 26 | 9 | 7/1330 (0.5%) | NT* |
| SR1x04TDNT000002-003 short repeat | 50 | 30 | 18 | 25 | 9/1355 (0.66%) | NT* |
| SR1x04TDNT000003-002 short repeat | 50 | 20 | 21 | 25 | 24/1389 (1.7%) | NT* |
| SR1x04TDNT000007-003 long repeat | 50 | 25 | 25 | 17 | 3/1346 (0.2%) | NT* |

*NT: not tested yet

Moreover all $PPT^R$ and $GFP^F$ seedlings are indeed hygromycin sensitive, demonstrating the hyg gene has indeed been removed by intrachromosomal recombination in the IHR locus.

| Cross | N° of $Hyg^R$ seedlings/N° of $PPT^R$ and $GFP^F$ seedlings screened for $Hyg^R$ |
|---|---|
| SR1x04TDNT000012-003 | 0/11 |
| SR1x04TDNT000008-001 | 0/12 |
| SR1x04TDNT000008-003 | 0/11 |
| SR1x04TDNT000001-002 | 0/8 |
| SR1x04TDNT000005-003 | 0/7 |
| SR1x04TDNT000006-003 | 0/7 |

From the segregation analysis of 18 progeny populations, it can be concluded that there is a very strong effect of NTM19-I-SceI on the frequency of IHR during transition from one generation to another as all $PPT^R$ seedlings are also $Km^R$.

The progeny of a crossing between SR1 (female) and 04TDNT00000X-00Y will normally segregate into:

25% with only NTM19-ISceI endonuclease

25% with only the HR construct

25% with both NTM19-I-SceI endonuclease+IHR construct

25% neither NTM19-I-SceI endonuclease nor IHR construct

The fact that all $PPT^R$ seedlings are also $Km^R$ shows that all HR recombinants occur only in the fraction which contains both the I-SceI endonuclease under control of a NTM19 microspore specific promoter as well as the HR construct. Our results show that in the best case up to 11% of the microspores which contain both NTM19-ISceI endonuclease+IHR construct has undergone intrachromosomal homologous recombination resulting in the restoration of a defective egfp-bar fusion gene (SR1×04TDNT000006-001). As no IHR recombinants resulting in a functional egfp-bar gene were obtained in the fraction which contain only the IHR construct, we may conclude that either spontaneous IHR (in absence of targeted DSB induction in the microspores) does not occur or if spontaneous IHR does occur, it does not result in the restoration of a defective egfp-bar fusion gene. In contrast, DSB-induced IHR in the microspores allows more precise intrachromosomal homologous recombination resulting in the restoration of a defective egfp-bar fusion gene.

Sequence analysis showed that no footprints are left after removal of the selectable marker mediated by DSB-induced IHR in the microspores.

The invention claimed is:

1. A method for exchanging a target DNA sequence in the genome of a plant for a DNA sequence of interest comprising:

a. inducing a first double stranded DNA break at a preselected site in the genome of a cell of a plant, said preselected site being located within said target DNA sequence or in the vicinity of said target DNA sequence;

b. introducing a repair DNA molecule into said plant cell, said DNA molecule comprising i. said DNA sequence of interest located between two flanking DNA regions having at least 80% sequence homology to a DNA region flanking said target DNA sequence, and flanking said preselected site in the genome of said plant cell;

ii. a selectable or screenable marker gene located between said flanking DNA regions, said selectable or screenable marker gene further being located between one of the flanking DNA regions and another copy of at least part of said one of the flanking DNA regions immediately adjacent to the target DNA sequence located in direct repeat; and iii. a recognition site for a DSBI enzyme located between said one of the flanking DNA regions and said partial flanking DNA region located in direct repeat;

c. selecting a population of plant cells comprising said selectable or screenable marker;

d. selecting a plant cell wherein said selectable or screenable marker has been introduced by homologous recombination through said flanking DNA regions and regenerating a plant from said plant cell;

e. crossing said regenerated plant or a progeny plant thereof comprising said selectable marker gene with a plant comprising a DSBI enzyme encoding chimeric gene, said chimeric gene comprising the following operably linked DNA segments:

i. a microspore specific promoter;

ii. a DNA region encoding a double stranded DNA break inducing (DSBI) enzyme recognizing said recognition site located in said DNA of interest;

iii. a transcription termination and polyadenylation region;

f. selecting a progeny plant (F1-plant) comprising said selectable or screenable marker gene and said DSBI enzyme encoding chimeric gene;

g. crossing said progeny plant with another plant whereby said progeny plant is used as pollen donor;

h. selecting a population of progeny plants (F2-population) which comprises said DSBI enzyme encoding chimeric gene; and i. selecting a progeny plant wherein said selectable or screenable marker gene is deleted by homologous recombination between said one of the flanking DNA regions and said another copy of at least part of said one of the flanking DNA regions immediately adjacent to the target DNA sequence, located in direct repeat.

2. The method of claim 1 wherein said first double stranded break at said preselected site is induced by introduction of a first DSBI enzyme, said first DSBI enzyme not recognizing said recognition site for a DSBI enzyme located in said DNA of interest.

3. The method of claim 2, wherein said first DSBI enzyme and said DSBI enzyme recognizing said recognition site located in said DNA of interest are two different DSBI enzymes, wherein said enzymes are I-Sce I, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-DhaI, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, PI-Tsp I, or a chimeric endonuclease comprising a Zn finger DNA binding domain and a DNA cleavage domain.

4. The method of claim 1, wherein said DSBI enzyme recognizing said recognition site for a DSBI enzyme located in said DNA of interest is I-Sce I.

5. The method of claim 4, wherein said DNA region encoding said double stranded DNA break inducing enzyme comprises the nucleotide sequence of SEQ ID No 1 or SEQ ID No 2.

6. The method of claim 1, wherein said microspore specific promoter comprises a promoter comprising the nucleotide sequence of SEQ ID No 3 or a functional fragment thereof.

7. The method of claim 1, wherein said DSBI encoding chimeric gene comprises the nucleotide sequence of SEQ ID No. 6 from nucleotide 1941 to 3913.

8. A DNA vector for exchanging a target DNA sequence in the genome of a plant cell for a DNA sequence of interest through the induction of a double stranded break at a preselected site within said target sequence or in the vicinity thereof, said DNA vector comprising:

a. said DNA sequence of interest located between two flanking DNA regions having at least 80% sequence homology to a DNA region flanking said target DNA sequence and flanking said preselected site;

b. a selectable or screenable marker gene located between said flanking DNA regions, said selectable or screenable marker gene further being located between one of the flanking DNA regions and a partial flanking DNA region comprising part of said one of the flanking DNA regions immediately adjacent to the target DNA sequence located in direct repeat; and c. a recognition site for a double stranded DNA break inducing (DSBI) enzyme located between said one of the flanking DNA regions and said partial flanking DNA region located in direct repeat.

9. The method of claim 1, wherein the preselected site is located within said target DNA.

10. The method of claim 1, wherein the preselected site is located within 500 bp from the directly repeated DNA sequences.

11. The method of claim 1, wherein direct repeats immediately precede and follow the selectable or screenable marker gene.

12. The method of claim 11, wherein the direct repeats are identical.

13. The method of claim 10, wherein direct repeats immediately precede and follow the selectable or screenable marker gene.

14. The method of claim 13, wherein the direct repeats are identical.

* * * * *

SEQUENCE LISTING

<160> NUMBER OF SEQ ID NOS: 6

<210> SEQ ID NO 1
<211> LENGTH: 732
<212> TYPE: DNA
<213> ORGANISM: Artificial Sequence
<220> FEATURE:
<223> OTHER INFORMATION: synthetic I-SceI coding region (UIPAC)
<220> FEATURE:
<221> NAME/KEY: variation
<222> LOCATION: (25)..(27)
<223> OTHER INFORMATION: AGA
<220> FEATURE:
<221> NAME/KEY: variation
<222> LOCATION: (73)..(75)
<223> OTHER INFORMATION: AGC
<220> FEATURE:
<221> NAME/KEY: variation
<222> LOCATION: (97)..(99)
<223> OTHER INFORMATION: AGC
<220> FEATURE:
<221> NAME/KEY: variation
<222> LOCATION: (169)..(171)
<223> OTHER INFORMATION: AGA
<220> FEATURE:
<221> NAME/KEY: variation
<222> LOCATION: (172)..(174)
<223> OTHER INFORMATION: AGC
<220> FEATURE:
<221> NAME/KEY: variation
<222> LOCATION: (175)..(177)
<223> OTHER INFORMATION: AGA
<220> FEATURE:
<221> NAME/KEY: variation
<222> LOCATION: (268)..(270)
<223> OTHER INFORMATION: AGC
<220> FEATURE:
<221> NAME/KEY: variation
<222> LOCATION: (289)..(291)
<223> OTHER INFORMATION: AGA
<220> FEATURE:
<221> NAME/KEY: variation
<222> LOCATION: (436)..(438)
<223> OTHER INFORMATION: AGC
<220> FEATURE:
<221> NAME/KEY: variation
<222> LOCATION: (490)..(492)
<223> OTHER INFORMATION: AGC
<220> FEATURE:
<221> NAME/KEY: variation
<222> LOCATION: (502)..(504)
<223> OTHER INFORMATION: AGC
<220> FEATURE:
<221> NAME/KEY: variation
<222> LOCATION: (523)..(525)
<223> OTHER INFORMATION: AGC
<220> FEATURE:
<221> NAME/KEY: variation
<222> LOCATION: (565)..(567)
<223> OTHER INFORMATION: AGA
<220> FEATURE:
<221> NAME/KEY: variation
<222> LOCATION: (631)..(633)
<223> OTHER INFORMATION: AGC
<220> FEATURE:
<221> NAME/KEY: variation
<222> LOCATION: (637)..(639)
<223> OTHER INFORMATION: AGC
<220> FEATURE:
<221> NAME/KEY: variation
<222> LOCATION: (712)..(714)
<223> OTHER INFORMATION: AGC
<220> FEATURE:
<221> NAME/KEY: variation
<222> LOCATION: (715)..(717)
<223> OTHER INFORMATION: AGC -continued

<400> SEQUENCE: 1

```
atggcyaarc chcchaaraa raarcgsaaa gtsaacatya araaraacca ggtsatgaac     60

ctsggmccha actcmaarct sctsaargag tacaartcmc arctsatyga rctsaacaty    120

garcarttcg argcyggmat cggmctsaty ctsggmgayg cytacatycg stcmcgsgay    180

garggmaara cytactgyat gcagttcgar tggaaraaca argcytacat ggaycaygts    240

tgyctsctst acgaycartg ggtsctstcm cchcchcaya araargarcg sgtsaaccay    300

ctsggmaacc tsgtsatyac ytggggmgcy caracyttca arcaycargc yttcaacaar    360

ctsgcsaacc tsttcatyct saacaacaar aaracyatyc chaacaacct sgtsgaraac    420

tacctsacyc cyatgtcmct sgcytactgg ttcatggayg ayggmggmaa rtgggaytac    480

aacaaraact cmacyaacaa rtcmatygts ctsaacacyc artcmttcac yttcgargar    540

gtsgartacc tsgtsaargg mctscgsaac aarttccarc tsaactgyta cgtsaagaty    600

aacaaraaca arccyatyat ctacatygay tcmatgtcmt acctsatytt ctacaaccts    660

atyaarccht acctsatycc hcaratgatg tacaarctsc chaacacyat ytcmtcmgar    720

acyttcctsa ar                                                        732
```

<210> SEQ ID NO 2
<211> LENGTH: 732
<212> TYPE: DNA
<213> ORGANISM: Artificial Sequence
<220> FEATURE:
<223> OTHER INFORMATION: synthetic I-SceI coding region

<400> SEQUENCE: 2

```
atggccaagc ctcccaagaa gaagcgcaaa gtgaacatca agaagaacca ggtgatgaac     60

ctgggaccta acagcaagct cctgaaggag tacaagagcc agctgatcga actgaacatc    120

gagcagttcg aagctggcat cggcctgatc ctgggcgatg cctacatcag atcccgggac    180

gaaggcaaga cctactgcat gcagttcgag tggaagaaca aggcctacat ggaccacgtg    240

tgtctgctgt acgaccagtg ggtcctgagc cctcctcaca agaaggagcg cgtgaaccat    300

ctgggcaacc tcgtgatcac ctggggagcc cagaccttca agcaccaggc cttcaacaag    360

ctggccaacc tgttcatcgt gaacaacaag aagaccatcc ccaacaacct cgtggagaac    420

tacctcactc ccatgagcct ggcctactgg ttcatggacg acggaggcaa gtgggactac    480

aacaagaaca gcaccaacaa gtcaattgtg ctgaacaccc aaagcttcac cttcgaagaa    540

gtggagtacc tcgtcaaggg cctgcgcaac aagttccagc tgaactgcta cgtgaagatc    600

aacaagaaca agcctatcat ctacatcgac agcatgagct acctgatctt ctacaacctg    660

atcaagccat acctgatccc tcagatgatg tacaagctgc ccaacaccat cagcagcgag    720

accttcctga ag                                                        732
```

<210> SEQ ID NO 3
<211> LENGTH: 1618
<212> TYPE: DNA
<213> ORGANISM: Nicotiana tabacum
<220> FEATURE:
<221> NAME/KEY: TATA_signal
<222> LOCATION: (919)..(922)
<220> FEATURE:
<221> NAME/KEY: mRNA
<222> LOCATION: (954)..(1573)
<220> FEATURE:
<221> NAME/KEY: gene
<222> LOCATION: (993)..(1271)
<223> OTHER INFORMATION: NTM19
<220> FEATURE:

<221> NAME/KEY: misc_feature
<222> LOCATION: (993)..(1271)
<223> OTHER INFORMATION: coding region

<400> SEQUENCE: 3
gatccagatt tatagggtcc taatgcgggt actgaacacc aggtgggaaa caaaaaatat 60
acagaacaac tcctttagaa tttacaattt ttgagcgtgt tggcttggta cgattctact 120
tttcatatct ctcgtcatct cctaactcct atggttcacc agccaccgat taattatgac 180
accgctaaca aaaatcttgc gacgacattg agagaaattt cttttcataa attggtaatt 240
cgtacatcat ttataggcgt tagctataac cttttagtta gtgaatacaa tactttttgc 300
tattattatg taacttttag atatgaattt actttcaaaa aaaaaaaaag gatcgatgtt 360
ggttatcaac taaggaccaa ccactttgga cgtctcacca ctaagttaaa taaatcactt 420
tgttctcgaa aaaaacccca aaagtgttaa aatgcttttc atatcataat caaacaacgt 480
gattaataaa atctattaag ttaatagaag tagggaataa atcgggcaaa agaatttgat 540
acaaaccaaa ccggtcaaaa aagctagtat tcatataaat ggactataca agttaatacc 600
agctagcaga aattaaatag tttattaagt tgattacaaa acaattcctc atttaaaaaa 660
agttaatgta atcaagagat cttttgcttc taattgatca gacgaggacc cctcttattt 720
attttctttt tcatataaga ttttgaatag atatagggaa atcttgttca ctctttatct 780
acttcaaatt gcatgcattt taagaattct ctttgtatgc aaacttcagt atttatgatt 840
gacataaatc aatattcata tcttcgataa agttaataac tctcctaata cttatgaata 900
tctcttcctt tacaacccta taaaaccccc cactatagct accttcataa ttcatcttag 960
agtaccaacc ctaaatttct tagtgattaa ccatggctaa gaaaagtctc actttctca 1020 tttgcatttt cctacttctc aatttatgtt ttgcaattga gaacgtagaa actatgcaaa 1080
aatcggattc atcgtcacaa gataaagaat tagattggtt tcatccgtgg ttccatccac 1140
atccatggtg gctacatcca catccatggc cattcgttca tccgccaatg ccagctggcg 1200
gttttcatca tgcatggcca ttcccccatc caccgatgcc tgctggtggt tttaagtttc 1260
ctcatcaata atttcatcgt catccatggc cattcatgca tccaccagtt ccatctccac 1320
ctaaaggaga caagaattaa ttgaaaatat gaagagaagt gttggatcaa catcttattg 1380
atcacatatt tttctttagg ttaatatctt taggatttat gtcttaggtt atttttgata 1440
aaaattaaaa taaatgatcg ttctagggta gttattataa tttcttagat ttttccaagt 1500
agctttcgat ggtagaaatg ttattaattt gattcggctt atcatgaaat aaaatccgta 1560
gtattattgc tttagctttt atgatttgta gttattttat gttgattgtt ctccattt 1618

<210> SEQ ID NO 4
<211> LENGTH: 4683
<212> TYPE: DNA
<213> ORGANISM: Artificial Sequence
<220> FEATURE:
<223> OTHER INFORMATION: T-DNA of pTCV63
<220> FEATURE:
<221> NAME/KEY: misc_feature
<222> LOCATION: (191)..(222)
<223> OTHER INFORMATION: Right T-DNA border
<220> FEATURE:
<221> NAME/KEY: misc_feature
<222> LOCATION: (270)..(818)
<223> OTHER INFORMATION: CaMV35S promoter region
<220> FEATURE:
<221> NAME/KEY: misc_feature
<222> LOCATION: (819)..(875)
<223> OTHER INFORMATION: Cab22Leader sequence
<220> FEATURE:

-continued

<221> NAME/KEY: misc_feature
<222> LOCATION: (885)..(1391)
<223> OTHER INFORMATION: 5' part of the eGFP coding region
<220> FEATURE:
<221> NAME/KEY: misc_feature
<222> LOCATION: (1392)..(1409)
<223> OTHER INFORMATION: I-SceI recognition site
<220> FEATURE:
<221> NAME/KEY: misc_feature
<222> LOCATION: (1411)..(1419)
<223> OTHER INFORMATION: Zif268 recognition site
<220> FEATURE:
<221> NAME/KEY: misc_feature
<222> LOCATION: (1433)..(1671)
<223> OTHER INFORMATION: 3' 35S polyadenylation region (complement)
<220> FEATURE:
<221> NAME/KEY: misc_feature
<222> LOCATION: (1683)..(2708)
<223> OTHER INFORMATION: hygromycin resistance coding region
(complement)
<220> FEATURE:
<221> NAME/KEY: misc_feature
<222> LOCATION: (2715)..(2787)
<223> OTHER INFORMATION: CsVMV leader region (complement)
<220> FEATURE:
<221> NAME/KEY: misc_feature
<222> LOCATION: (2788)..(3227)
<223> OTHER INFORMATION: CsVMV promoter fragment (complement)
<220> FEATURE:
<221> NAME/KEY: misc_feature
<222> LOCATION: (3269)..(3787)
<223> OTHER INFORMATION: 3' part of eGFP
<220> FEATURE:
<221> NAME/KEY: misc_feature
<222> LOCATION: (3788)..(4339)
<223> OTHER INFORMATION: phosphinotricin acetyltransferase coding region
<220> FEATURE:
<221> NAME/KEY: misc_feature
<222> LOCATION: (4341)..(4549)
<223> OTHER INFORMATION: 3' nos: transcription termination and
polyadenylation region
<220> FEATURE:
<221> NAME/KEY: misc_feature
<222> LOCATION: (4659)..(4683)
<223> OTHER INFORMATION: right T-DNA border

<400> SEQUENCE: 4
agattcgaag ctcggtcccg tgggtgttct gtcgtctcgt tgtacaacga aatccattcc 60
cattccgcgc tcaagatggc ttcccctcgg cagttcatca gggctaaatc aatctagccg 120
acttgtccgg tgaaatgggc tgcactccaa cagaaacaat caaacaaaca tacacagcga 180
cttattcaca cgcgacaaat tacaacggta tatatcctgc cagtactcgg ccgtcgacct 240
gcaggcaatt ggtacctacg tatgcatggc gcgccatatg caccatacat ggagtcaaaa 300
attcagatcg aggatctaac agaactcgcc gtgaagactg gcgaacagtt catacagagt 360
cttttacgac tcaatgacaa gaagaaaatc ttcgtcaaca tggtggagca cgacactctc 420
gtctactcca agaatatcaa agatacagtc tcagaagacc aaagggctat tgagactttt 480
caacaaaggg taatatcggg aaacctcctc ggattccatt gcccagctat ctgtcacttc 540
atcaaaagga cagtagaaaa ggaaggtggc acctacaaat gccatcattg cgataaagga 600
aaggctatcg ttcaagatgc ctctgccgac agtggtccca aagatggacc cccacccacg 660
aggagcatcg tggaaaaaga agacgttcca accacgtctt caaagcaagt ggattgatgt 720
gatatctcca ctgacgtaag ggatgacgca caatcccact atccttcgca agacccttcc 780
tctatataag gaagttcatt tcatttggag aggactcgag ctcatttctc tattacttca 840
gccataacaa aagaactctt ttctcttctt attaaaccaa aaccatggtg agcaagggcg 900
aggagctgtt caccggggtg gtgcccatcc tggtcgagct ggacggcgac gtaaacggcc 960

-continued acaagttcag cgtgtccggc gagggcgagg gcgatgccac ctacggcaag ctgaccctga 1020
agttcatctg caccaccggc aagctgcccg tgccctggcc caccctcgtg accaccctga 1080
cctacggcgt gcagtgcttc agccgctacc ccgaccacat gaagcagcac gacttcttca 1140
agtccgccat gcccgaaggc tacgtccagg agcgcaccat cttcttcaag gacgacggca 1200
actacaagac ccgcgccgag gtgaagttcg agggcgacac cctggtgaac cgcatcgagc 1260
tgaagggcat cgacttcaag gaggacggca acatcctggg gcacaagctg gagtacaact 1320
acaacagcca caacgtctat atcatggccg acaagcagaa gaacggcatc aaggtgaact 1380
tcaagatccg ctagggataa cagggtaatg gcgtgggcga ccggtcccgg ccgctgtacc 1440
atgcatgatc tggattttag tactggattt tggttttagg aattagaaat tttattgata 1500
gaagtatttt acaaatacaa atacatacta agggtttctt atatgctcaa cacatgagcg 1560
aaaccctata ggaaccctaa ttcccttatc tgggaactac tcacacatta ttatggagaa 1620
aatagagaga gatagatttg tagagagaga ctggtgattt cagcgtgtcc aagcttgata 1680
tcctattcct ttgccctcgg acgagtgctg gggcgtcggt ttccactatc ggcgagtact 1740
tctacacagc catcggtcca gacggccgcg cttctgcggg cgatttgtgt acgcccgaca 1800
gtcccggctc cggatcggac gattgcgtcg catcgaccct gcgcccaagc tgcatcatcg 1860
aaattgccgt caaccaagct ctgatagagt tggtcaagac caatgcggag catatacgcc 1920
cggagccgcg gcgatcctgc aagctccgga tgcctccgct cgaagtagcg cgtctgctgc 1980
tccatacaag ccaaccacgg cctccagaag aagatgttgg cgacctcgta ttgggaatcc 2040
ccgaacatcg cctcgctcca gtcaatgacc gctgttatgc ggccattgtc cgtcaggaca 2100
ttgttggagc cgaaatccgc gtgcacgagg tgccggactt cggggcagtc ctcggcccaa 2160
agcatcagct catcgagagc ctgcgcgacg gacgcactga cggtgtcgtc catcacagtt 2220
tgccagtgat acacatgggg atcagcaatc gcgcatatga aatcacgcca tgtagtgtat 2280
tgaccgattc cttgcggtcc gaatgggccg aacccgctcg tctggctaag atcggccgca 2340
gcgatcgcat ccatggcctc cgcgaccggc tgcagaacag cgggcagttc ggtttcaggc 2400
aggtcttgca acgtgacacc ctgtgcacgg cgggagatgc aataggtcag gctctcgctg 2460
aattccccaa tgtcaagcac ttccggaatc gggagcgcgg ccgatgcaaa gtgccgataa 2520
acataacgat ctttgtagaa accatcggcg cagctattta cccgcaggac atatccacgc 2580
cctcctacat cgaagctgaa agcacgagat tcttcgccct ccgagagctg catcaggtcg 2640
gagacgctgt cgaacttttc gatcagaaac ttctcgacag acgtcgcggt gagttcaggc 2700
tttttcatct cgagacaaac ttacaaattt ctctgaagtt gtatcctcag tacttcaaag 2760
aaaatagctt acaccaaatt ttttcttgtt ttcacaaatg ccgaacttgg ttccttatat 2820
aggaaaactc aagggcaaaa atgacacgga aaaatataaa aggataagta gtgggggata 2880
agattccttt gtgataaggt tactttccgc ccttacattt tccaccttac atgtgtcctc 2940
tatgtctctt tcacaatcac cgaccttatc ttcttctttt cattgttgtc gtcagtgctt 3000
acgtcttcaa gattcttttc ttcgcctggt tcttcttttt caatttctac gtattcttct 3060
tcgtattctg gcagtatagg atcttgtatc tgtacattct tcatttttga acataggttg 3120
catatgtgcc gcatattgat ctgcttcttg ctgagctcac ataatacttc catagttttt 3180
cccgtaaaca ttggattctt gatgctacat cttggataat taccttcggc gcgccatgca 3240
tacgtaggta ccaattgccg ggaccggtta cggcgtgcag tgcttcagcc gctaccccga 3300
ccacatgaag cagcacgact tcttcaagtc cgccatgccc gaaggctacg tccaggagcg 3360

-continued

```
caccatcttc ttcaaggacg acggcaacta caagacccgc gccgaggtga agttcgaggg   3420

cgacaccctg gtgaaccgca tcgagctgaa gggcatcgac ttcaaggagg acggcaacat   3480

cctggggcac aagctggagt acaactacaa cagccacaac gtctatatca tggccgacaa   3540

gcagaagaac ggcatcaagg tgaacttcaa gatccgccac aacatcgagg acggcagcgt   3600

gcagctcgcc gaccactacc agcagaacac ccccatcggc gacggccccg tgctgctgcc   3660

cgacaaccac tacctgagca cccagtccgc cctgagcaaa gaccccaacg agaagcgcga   3720

tcacatggtc ctgctggagt tcgtgaccgc cgccgggatc actctcggca tggacgagct   3780

gtacaagatg gacccagaac gacgcccggc cgacatccgc cgtgccaccg aggcggacat   3840

gccggcggtc tgcaccatcg tcaaccacta catcgagaca agcacggtca acttccgtac   3900

cgagccgcag gaaccgcagg agtggacgga cgacctcgtc cgtctgcggg agcgctatcc   3960

ctggctcgtc gccgaggtgg acggcgaggt cgccggcatc gcctacgcgg gcccctggaa   4020

ggcacgcaac gcctacgact ggacggccga gtcgaccgtg tacgtctccc cccgccacca   4080

gcggacggga ctgggctcca cgctctacac ccacctgctg aagtccctgg aggcacaggg   4140

cttcaagagc gtggtcgctg tcatcgggct gcccaacgac ccgagcgtgc gcatgcacga   4200

ggcgctcgga tatgcccccc gcggcatgct gcgggcggcc ggcttcaagc acgggaactg   4260

gcatgacgtg ggtttctggc agctggactt cagcctgccg gtaccgcccc gtccggtcct   4320

gcccgtcacc gagatctgag ctagcacgcg tctaggatcc gaagcagatc gttcaaacat   4380

ttggcaataa agtttcttaa gattgaatcc tgttgccggt cttgcgatga ttatcatata   4440

atttctgttg aattacgtta agcatgtaat aattaacatg taatgcatga cgttatttat   4500

gagatgggtt tttatgatta gagtcccgca attatacatt taatacgcga tagaaaacaa   4560

aatatagcgc gcaaactagg ataaattatc gcgcgcggtg tcatctatgt tactagatcg   4620

ggaagatcct ctagatacgt agcgatcgcc atggagccat ttacaattga atatatcctg   4680

ccg                                                                 4683
```

<210> SEQ ID NO 5
<211> LENGTH: 4992
<212> TYPE: DNA
<213> ORGANISM: Artificial Sequence
<220> FEATURE:
<223> OTHER INFORMATION: T-DNA of pTCV64
<220> FEATURE:
<221> NAME/KEY: misc_feature
<222> LOCATION: (191)..(222)
<223> OTHER INFORMATION: Right T-DNA border
<220> FEATURE:
<221> NAME/KEY: misc_feature
<222> LOCATION: (270)..(818)
<223> OTHER INFORMATION: CaMV35S promoter fragment
<220> FEATURE:
<221> NAME/KEY: misc_feature
<222> LOCATION: (819)..(875)
<223> OTHER INFORMATION: cab22Leader fragment
<220> FEATURE:
<221> NAME/KEY: misc_feature
<222> LOCATION: (885)..(1553)
<223> OTHER INFORMATION: 5' part of eGFP coding region
<220> FEATURE:
<221> NAME/KEY: misc_feature
<222> LOCATION: (1554)..(1571)
<223> OTHER INFORMATION: I-SceI recognition site
<220> FEATURE:
<221> NAME/KEY: misc_feature
<222> LOCATION: (1573)..(1581)
<223> OTHER INFORMATION: Zif268 recognition site
<220> FEATURE:
<221> NAME/KEY: misc_feature
<222> LOCATION: (1595)..(1833)

<223> OTHER INFORMATION: 3' 35S transcription termination and
      polyadenylation region (complement)
<220> FEATURE:
<221> NAME/KEY: misc_feature
<222> LOCATION: (1845)..(2870)
<223> OTHER INFORMATION: hygromycin phosphotransferase coding region
<220> FEATURE:
<221> NAME/KEY: misc_feature
<222> LOCATION: (2877)..(2949)
<223> OTHER INFORMATION: leader of CsVMV (complement)
<220> FEATURE:
<221> NAME/KEY: misc_feature
<222> LOCATION: (2950)..(3389)
<223> OTHER INFORMATION: CsVMV promoter fragment (complement)
<220> FEATURE:
<221> NAME/KEY: misc_feature
<222> LOCATION: (3431)..(4096)
<223> OTHER INFORMATION: 3' part of eGFP coding region
<220> FEATURE:
<221> NAME/KEY: misc_feature
<222> LOCATION: (4097)..(4648)
<223> OTHER INFORMATION: phosphinotricin acetyltransferase coding region
<220> FEATURE:
<221> NAME/KEY: misc_feature
<222> LOCATION: (4650)..(4858)
<223> OTHER INFORMATION: 3'nos: transcription termination and
      polyadenylation region of the nopaline synthase gene
<220> FEATURE:
<221> NAME/KEY: misc_feature
<222> LOCATION: (4968)..(4992)
<223> OTHER INFORMATION: Left T-DNA border sequence

<400> SEQUENCE: 5
agattcgaag ctcggtcccg tgggtgttct gtcgtctcgt tgtacaacga aatccattcc 60
cattccgcgc tcaagatggc ttcccctcgg cagttcatca gggctaaatc aatctagccg 120
acttgtccgg tgaaatgggc tgcactccaa cagaaacaat caaacaaaca tacacagcga 180
cttattcaca cgcgacaaat tacaacggta tatatcctgc cagtactcgg ccgtcgacct 240
gcaggcaatt ggtacctacg tatgcatggc gcgccatatg caccatacat ggagtcaaaa 300
attcagatcg aggatctaac agaactcgcc gtgaagactg gcgaacagtt catacagagt 360
cttttacgac tcaatgacaa gaagaaaatc ttcgtcaaca tggtggagca cgacactctc 420
gtctactcca agaatatcaa agatacagtc tcagaagacc aaagggctat tgagactttt 480
caacaaaggg taatatcggg aaacctcctc ggattccatt gcccagctat ctgtcacttc 540
atcaaaagga cagtagaaaa ggaaggtggc acctacaaat gccatcattg cgataaagga 600
aaggctatcg ttcaagatgc ctctgccgac agtggtccca aagatggacc cccacccacg 660
aggagcatcg tggaaaaaga agacgttcca accacgtctt caaagcaagt ggattgatgt 720
gatatctcca ctgacgtaag ggatgacgca caatcccact atccttcgca agacccttcc 780
tctatataag gaagttcatt tcatttggag aggactcgag ctcatttctc tattacttca 840
gccataacaa aagaactctt ttctcttctt attaaaccaa aaccatggtg agcaagggcg 900
aggagctgtt caccggggtg gtgcccatcc tggtcgagct ggacggcgac gtaaacggcc 960
acaagttcag cgtgtccggc gagggcgagg gcgatgccac ctacggcaag ctgaccctga 1020
agttcatctg caccaccggc aagctgcccg tgccctggcc caccctcgtg accaccctga 1080
cctacggcgt gcagtgcttc agccgctacc ccgaccacat gaagcagcac gacttcttca 1140
agtccgccat gcccgaaggc tacgtccagg agcgcaccat cttcttcaag gacgacggca 1200
actacaagac ccgcgccgag gtgaagttcg agggcgacac cctggtgaac cgcatcgagc 1260
tgaagggcat cgacttcaag gaggacggca acatcctggg gcacaagctg gagtacaact 1320
acaacagcca caacgtctat atcatggccg acaagcagaa gaacggcatc aaggtgaact 1380

-continued

```
tcaagatccg ccacaacatc gaggacggca gcgtgcagct cgccgaccac taccagcaga   1440
acacccccat cggcgacggc cccgtgctgc tgcccgacaa ccactacctg agcacccagt   1500
ccgccctgag caaagacccc aacgagaagc gcgatcacat ggtcctgctg gagtagggat   1560
aacagggtaa tggcgtgggc gaccggtccc ggccgctgta ccatgcatga tctggatttt   1620
agtactggat tttggtttta ggaattagaa attttattga tagaagtatt ttacaaatac   1680
aaatacatac taagggtttc ttatatgctc aacacatgag cgaaacccta taggaaccct   1740
aattccctta tctgggaact actcacacat tattatggag aaaatagaga gagatagatt   1800
tgtagagaga gactggtgat ttcagcgtgt ccaagcttga tatcctattc ctttgccctc   1860
ggacgagtgc tggggcgtcg gtttccacta tcggcgagta cttctacaca gccatcggtc   1920
cagacggccg cgcttctgcg ggcgatttgt gtacgcccga cagtcccggc tccggatcgg   1980
acgattgcgt cgcatcgacc ctgcgcccaa gctgcatcat cgaaattgcc gtcaaccaag   2040
ctctgataga gttggtcaag accaatgcgg agcatatacg cccggagccg cggcgatcct   2100
gcaagctccg gatgcctccg ctcgaagtag cgcgtctgct gctccataca agccaaccac   2160
ggcctccaga agaagatgtt ggcgacctcg tattgggaat ccccgaacat cgcctcgctc   2220
cagtcaatga ccgctgttat gcggccattg tccgtcagga cattgttgga gccgaaatcc   2280
gcgtgcacga ggtgccggac ttcggggcag tcctcggccc aaagcatcag ctcatcgaga   2340
gcctgcgcga cggacgcact gacggtgtcg tccatcacag tttgccagtg atacacatgg   2400
ggatcagcaa tcgcgcatat gaaatcacgc catgtagtgt attgaccgat tccttgcggt   2460
ccgaatgggc cgaacccgct cgtctggcta agatcggccg cagcgatcgc atccatggcc   2520
tccgcgaccg gctgcagaac agcgggcagt tcggtttcag gcaggtcttg caacgtgaca   2580
ccctgtgcac ggcgggagat gcaataggtc aggctctcgc tgaattcccc aatgtcaagc   2640
acttccggaa tcgggagcgc ggccgatgca aagtgccgat aaacataacg atctttgtag   2700
aaaccatcgg cgcagctatt tacccgcagg acatatccac gccctcctac atcgaagctg   2760
aaagcacgag attcttcgcc ctccgagagc tgcatcaggt cggagacgct gtcgaacttt   2820
tcgatcagaa acttctcgac agacgtcgcg gtgagttcag gctttttcat ctcgagacaa   2880
acttacaaat ttctctgaag ttgtatcctc agtacttcaa agaaaatagc ttacaccaaa   2940
tttttcttg ttttcacaaa tgccgaactt ggttccttat ataggaaaac tcaagggcaa   3000
aaatgacacg gaaaaatata aaaggataag tagtggggga taagattcct ttgtgataag   3060
gttactttcc gcccttacat tttccacctt acatgtgtcc tctatgtctc tttcacaatc   3120
accgacctta tcttcttctt ttcattgttg tcgtcagtgc ttacgtcttc aagattcttt   3180
tcttcgcctg gttcttcttt ttcaatttct acgtattctt cttcgtattc tggcagtata   3240
ggatcttgta tctgtacatt cttcattttt gaacataggt tgcatatgtg ccgcatattg   3300
atctgcttct tgctgagctc acataatact tccatagttt ttcccgtaaa cattggattc   3360
ttgatgctac atcttggata attaccttcg gcgcgccatg catacgtagg taccaattgc   3420
cgggaccggt gagctggacg gcgacgtaaa cggccacaag ttcagcgtgt ccggcgaggg   3480
cgagggcgat gccacctacg gcaagctgac cctgaagttc atctgcacca ccggcaagct   3540
gcccgtgccc tggcccaccc tcgtgaccac cctgacctac ggcgtgcagt gcttcagccg   3600
ctaccccgac cacatgaagc agcacgactt cttcaagtcc gccatgcccg aaggctacgt   3660
ccaggagcgc accatcttct tcaaggacga cggcaactac aagacccgcg ccgaggtgaa   3720
gttcgagggc gacaccctgg tgaaccgcat cgagctgaag ggcatcgact tcaaggagga   3780
```

-continued

```
cggcaacatc ctggggcaca agctggagta caactacaac agccacaacg tctatatcat   3840

ggccgacaag cagaagaacg gcatcaaggt gaacttcaag atccgccaca acatcgagga   3900

cggcagcgtg cagctcgccg accactacca gcagaacacc cccatcggcg acggccccgt   3960

gctgctgccc gacaaccact acctgagcac ccagtccgcc ctgagcaaag accccaacga   4020

gaagcgcgat cacatggtcc tgctggagtt cgtgaccgcc gccgggatca ctctcggcat   4080

ggacgagctg tacaagatgg acccagaacg acgcccggcc gacatccgcc gtgccaccga   4140

ggcggacatg ccggcggtct gcaccatcgt caaccactac atcgagacaa gcacggtcaa   4200

cttccgtacc gagccgcagg aaccgcagga gtggacggac gacctcgtcc gtctgcggga   4260

gcgctatccc tggctcgtcg ccgaggtgga cggcgaggtc gccggcatcg cctacgcggg   4320

cccctggaag gcacgcaacg cctacgactg gacggccgag tcgaccgtgt acgtctcccc   4380

ccgccaccag cggacgggac tgggctccac gctctacacc cacctgctga agtccctgga   4440

ggcacagggc ttcaagagcg tggtcgctgt catcgggctg cccaacgacc cgagcgtgcg   4500

catgcacgag gcgctcggat atgccccccg cggcatgctg cgggcggccg gcttcaagca   4560

cgggaactgg catgacgtgg gtttctggca gctggacttc agcctgccgg taccgccccg   4620

tccggtcctg cccgtcaccg agatctgagc tagcacgcgt ctaggatccg aagcagatcg   4680

ttcaaacatt tggcaataaa gtttcttaag attgaatcct gttgccggtc ttgcgatgat   4740

tatcatataa tttctgttga attacgttaa gcatgtaata attaacatgt aatgcatgac   4800

gttatttatg agatgggttt ttatgattag agtcccgcaa ttatacattt aatacgcgat   4860

agaaaacaaa atatagcgcg caaactagga taaattatcg cgcgcggtgt catctatgtt   4920

actagatcgg gaagatcctc tagatacgta gcgatcgcca tggagccatt tacaattgaa   4980

tatatcctgc cg                                                        4992
```

<210> SEQ ID NO 6
<211> LENGTH: 3987
<212> TYPE: DNA
<213> ORGANISM: Artificial Sequence
<220> FEATURE:
<223> OTHER INFORMATION: T-DNA of pTCV72
<220> FEATURE:
<221> NAME/KEY: misc_feature
<222> LOCATION: (191)..(222)
<223> OTHER INFORMATION: right T-DNA border
<220> FEATURE:
<221> NAME/KEY: misc_feature
<222> LOCATION: (251)..(539)
<223> OTHER INFORMATION: 3'ocs: transcription termination and
polyadenylation region from an octopine synthase gene (complement)
<220> FEATURE:
<221> NAME/KEY: misc_feature
<222> LOCATION: (713)..(1510)
<223> OTHER INFORMATION: neomycin phosphotransferase II coding region
(complment)
<220> FEATURE:
<221> NAME/KEY: misc_feature
<222> LOCATION: (1511)..(1529)
<223> OTHER INFORMATION: linker sequence
<220> FEATURE:
<221> NAME/KEY: misc_feature
<222> LOCATION: (1530)..(1816)
<223> OTHER INFORMATION: nopaline synthase promoter fragment
(complement)
<220> FEATURE:
<221> NAME/KEY: misc_feature
<222> LOCATION: (1817)..(1929)
<223> OTHER INFORMATION: linker sequence
<220> FEATURE:
<221> NAME/KEY: misc_feature
<222> LOCATION: (1941)..(2926)
<223> OTHER INFORMATION: promoter fragment from NTM19 gene from tobacco
<220> FEATURE:
<221> NAME/KEY: misc_feature
<222> LOCATION: (2928)..(2961)
<223> OTHER INFORMATION: nuclear localization signal
<220> FEATURE:
<221> NAME/KEY: misc_feature
<222> LOCATION: (2962)..(3661)
<223> OTHER INFORMATION: I-SceI coding region
<220> FEATURE:
<221> NAME/KEY: misc_feature
<222> LOCATION: (3665)..(3913)
<223> OTHER INFORMATION: 3' 35S transcription termination and polyadenylation fragment
<220> FEATURE:
<221> NAME/KEY: misc_feature
<222> LOCATION: (3963)..(3987)
<223> OTHER INFORMATION: T-DNA left border region

<400> SEQUENCE: 6
agattcgaag ctcggtcccg tgggtgttct gtcgtctcgt tgtacaacga aatccattcc 60
cattccgcgc tcaagatggc ttcccctcgg cagttcatca gggctaaatc aatctagccg 120
acttgtccgg tgaaatgggc tgcactccaa cagaaacaat caaacaaaca tacacagcga 180
cttattcaca cgcgacaaat tacaacggta tatatcctgc cagtactcgg ccgtcgacct 240
gcaggcaatt gtttgttatt gtggcgctct atcatagatg tcgctataaa cctattcagc 300
acaatatatt gttttcattt taatattgta catataagta gtagggtaca atcagtaaat 360
tgaacggaga atattattca taaaaatacg atagtaacgg gtgatatatt cattagaatg 420
aaccgaaacc ggcggtaagg atctgagcta cacatgctca ggttttttac aacgtgcaca 480
acagaattga aagcaaatat catgcgatca taggcgtctc gcatatctca ttaaagcagg 540
gggtgggcga agaactccag catgagatcc ccgcgctgga ggatcatcca gccggcgtcc 600
cggaaaacga ttccgaagcc caacctttca tagaaggcgg cggtggaatc gaaatctcgt 660
gatggcaggt tgggcgtcgc ttggtcggtc atttcgaacc ccagagtccc gctcagaaga 720
actcgtcaag aaggcgatag aaggcgatgc gctgcgaatc gggagcggcg ataccgtaaa 780
gcacgaggaa gcggtcagcc cattcgccgc caagctcttc agcaatatca cgggtagcca 840
acgctatgtc ctgatagcgg tccgccacac ccagccggcc acagtcgatg aatccagaaa 900
agcggccatt ttccaccatg atattcggca agcaggcatc gccatgggtc acgacgagat 960
cctcgccgtc gggcatgcgc gccttgagcc tggcgaacag ttcggctggc gcgagcccct 1020
gatgctcttc gtccagatca tcctgatcga caagaccggc ttccatccga gtacgtgctc 1080
gctcgatgcg atgtttcgct tggtggtcga atgggcaggt agccggatca agcgtatgca 1140
gccgccgcat tgcatcagcc atgatggata ctttctcggc aggagcaagg tgagatgaca 1200
ggagatcctg ccccggcact tcgcccaata gcagccagtc ccttcccgct tcagtgacaa 1260
cgtcgagcac agctgcgcaa ggaacgcccg tcgtggccag ccacgatagc cgcgctgcct 1320
cgtcctgcag ttcattcagg gcaccggaca ggtcggtctt gacaaaaaga accgggcgcc 1380
cctgcgctga cagccggaac acggcggcat cagagcagcc gattgtctgt tgtgcccagt 1440
catagccgaa tagcctctcc acccaagcgg ccggagaacc tgcgtgcaat ccatcttgtt 1500
caatccacat gatcatgggc cggatctttg attgagagtg aatatgagac tctaattgga 1560
taccgagggg aatttatgga acgtcagtgg agcatttttg acaagaaata tttgctagct 1620
gatagtgacc ttaggcgact tttgaacgcg caataatggt ttctgacgta tgtgcttagc 1680
tcattaaact ccagaaaccc gcggctgagt ggctccttca atcgttgcgg ttctgtcagt 1740
tccaaacgta aaacggcttg tcccgcgtca tcggcggggg tcataacgtg actcccttaa 1800

-continued

```
ttctccgctc atgatcctgt ttcctgtgtg aaattgttat ccgctcacaa ttccacacat   1860
tatacgagcc ggaagcataa agtgtaaagc ctggggtgcc taatgagtga gaattgacgg   1920
gatctatggc gcgccatatg agatttatag ggtcctaatg cgggtactga acaccaggtg   1980
ggaaacaaaa aatatacaga acaactcctt tagaatttac aatttttgag cgtgttggct   2040
tggtacgatt ctacttttca tatctctcgt catctcctaa ctcctatggt tcaccagcca   2100
ccgattaatt atgacaccgc taacaaaaat cttgcgacga cattgagaga aatttctttt   2160
cataaattgg taattcgtac atcatttata ggcgttagct ataacctttt agttagtgaa   2220
tacaatactt tttgctatta ttatgtaact tttagatatg aatttacttt caaaaaaaaa   2280
aaaaggatcg atgttggtta tcaactaagg accaaccact ttggacgtct caccactaag   2340
ttaaataaat cactttgttc tcgaaaaaaa ccccaaaagt gttaaaatgc ttttcatatc   2400
ataatcaaac aacgtgatta ataaaatcta ttaagttaat agaagtaggg aataaatcgg   2460
gcaaaagaat ttgatacaaa ccaaaccggt caaaaaagct agtattcata taaatggact   2520
atacaagtta ataccagcta gcagaaatta aatagtttat taagttgatt acaaaacaat   2580
tcctcattta aaaaaagtta atgtaatcaa gagatctttt gcttctaatt gatcagacga   2640
ggacccctct tatttatttt ctttttcata taagattttg aatagatata gggaaatctt   2700
gttcactctt tatctacttc aaattgcatg cattttaaga attctctttg tatgcaaact   2760
tcagtattta tgattgacat aaatcaatat tcatatcttc gataaagtta ataactctcc   2820
taatacttat gaatatctct tcctttacaa ccctataaaa ccccccacta tagctacctt   2880
cataattcat cttagagtac caaccctaaa tttcttagtg attaaccatg gctaaacccc   2940
ccaagaagaa gcgcaaggtt aacatcaaaa aaaaccaggt aatgaacctg ggtccgaact   3000
ctaaactgct gaaagaatac aaatcccagc tgatcgaact gaacatcgaa cagttcgaag   3060
caggtatcgg tctgatcctg ggtgatgctt acatccgttc tcgtgatgaa ggtaaaacct   3120
actgtatgca gttcgagtgg aaaaacaaag catacatgga ccacgtatgt ctgctgtacg   3180
atcagtgggt actgtccccg ccgcacaaaa aagaacgtgt taaccacctg ggtaacctgg   3240
taatcacctg ggcgcccag actttcaaac accaagcttt caacaaactg gctaacctgt   3300
tcatcgttaa caacaaaaaa accatcccga acaacctggt tgaaaactac ctgaccccga   3360
tgtctctggc atactggttc atggatgatg gtggtaaatg ggattacaac aaaaactcta   3420
ccaacaaatc gatcgtactg aacacccagt ctttcacttt cgaagaagta gaatacctgg   3480
ttaagggtct gcgtaacaaa ttccaactga actgttacgt aaaaatcaac aaaaacaaac   3540
cgatcatcta catcgattct atgtcttacc tgatcttcta caacctgatc aaaccgtacc   3600
tgatcccgca gatgatgtac aaactgccga acactatctc ctccgaaact ttcctgaaat   3660
agggctagca agcttggaca cgctgaaatc accagtctct ctctacaaat ctatctctct   3720
ctattttctc cataataatg tgtgagtagt tcccagataa gggaattagg gttcctatag   3780
ggtttcgctc atgtgttgag catataagaa acccttagta tgtatttgta tttgtaaaat   3840
acttctatca ataaaatttc taattcctaa aaccaaaatc cagtactaaa atccagatca   3900
tgcatggtac agcggccgcg ttaacgcgta tactctagat acgtagcgat cgccatggag   3960
ccatttacaa ttgaatatat cctgccg                                       3987
```